United States Patent [19]

Allen et al.

[11] Patent Number: 5,100,897
[45] Date of Patent: Mar. 31, 1992

[54] SUBSTITUTED PYRIMIDINONES AS ANGIOTENSIN II ANTAGONISTS

[75] Inventors: Eric E. Allen, Edison; William J. Greenlee, Teaneck; Prasun K. Chakravarty, Edison; Arthur A. Patchett; Thomas F. Walsh, both of Westfield, all of N.J.

[73] Assignee: Merck & Co., Inc., Rahway, N.J.

[21] Appl. No.: 550,951

[22] Filed: Jul. 16, 1990

Related U.S. Application Data

[63] Continuation-in-part of Ser. No. 399,646, Aug. 28, 1989, abandoned.

[51] Int. Cl.⁵ .................. A61K 31/505; C07D 239/20; C07D 239/22
[52] U.S. Cl. .................... 514/269; 544/243; 544/319; 544/330; 544/331
[58] Field of Search .............. 544/310, 319, 243, 244, 544/327, 122, 123, 313, 314, 309, 317, 323, 324, 325, 331, 332, 330; 514/258, 269

[56] References Cited

U.S. PATENT DOCUMENTS 4,880,804 11/1989 Carini et al. .................... 514/234.5

FOREIGN PATENT DOCUMENTS 0234707 9/1987 European Pat. Off. ............ 544/321

OTHER PUBLICATIONS

Koller et al; Neuroscience Letters 14; 71, 1975.

*Primary Examiner*—Mukund J. Shah
*Assistant Examiner*—Y. N. Gupta
*Attorney, Agent, or Firm*—William H. Nicholson; Joseph F. DiPrima

[57] ABSTRACT

Novel substituted pyrimidinones of formula (I) which are useful as angiotensin II antagonists, are disclosed.

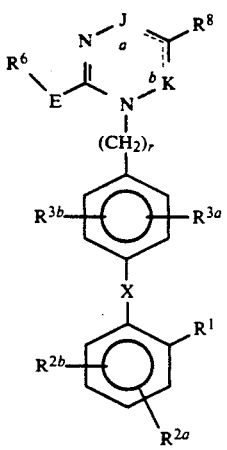

14 Claims, No Drawings

SUBSTITUTED PYRIMIDINONES AS ANGIOTENSIN II ANTAGONISTS

INTRODUCTION OF THE INVENTION

This is a continuation-in-part of copending application Ser. No. 399,646 filed Aug. 28, 1989, now abandoned.

This invention relates to novel substituted pyrimidinone compounds and derivatives thereof which are useful as angiotensin II antagonists in the treatment of elevated blood pressure, in the treatment of congestive heart failure, and in the treatment of elevated intraocular pressure. Thus, the substituted pyrimidinone compounds of the invention are useful as antihypertensives.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (A II), an octapeptide hormone is produced mainly in the blood during the cleavage of angiotensin I by angiotensin converting enzyme (ACE) localized on the endothelium of blood vessels of lung, kidney, and many other organs, and is the end product of the RAS A II is a powerful arterial vasoconstricter that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27-46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; 291,969; 323,841; and 324,377; and in articles by A. T. Chiu, et al. [*Eur. J. Pharm. Exp. Therap*, 157, 13-21 (1988)] and by P. C. Wong, et al. [*J. Pharm. Exp. Therap*, 247, 1-7(1988): *Hypertension*, 13, 489-497 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invention relates to novel substituted pyrimidinone compounds and derivatives thereof which are useful as angiotensin II antagonists and as antihypertensives, in the treatment of congestive heart failure, and in the treatment of elevated intraocular pressure. The compounds of this invention have the general formula (I):

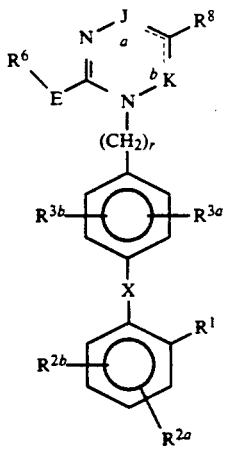

wherein:

J is —C(=M)— or

K is —C(=M)— or

provided that one and only one of J and K is —C(=M)—;

M is O or NR$^{21}$;

one of a and b is a double bond, provided that when J is —C(=M)— b is a double bond and when K is —C(=M)— a is a double bond;

R$^1$ is
 (a) —CO$_2$R$^4$,
 (b) —SO$_3$R$^5$,
 (c) —NHSO$_2$CF$_3$,
 (d) —PO(OR$^5$)$_2$,
 (e) —SO$_2$—NH—R$^9$,
 (f) —CONHOR$^5$,
 (g)

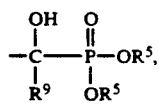

(h) —CN,
 (i) —PO(OR$^5$)R$^4$,
 (j)

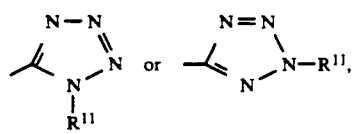

(k)

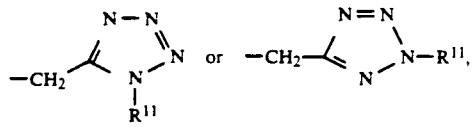

(l)

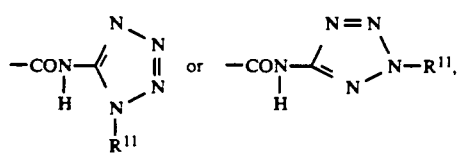

(m) —CONHNHSO$_2$CF$_3$,
(n)

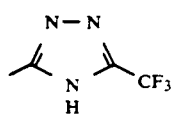

(o)

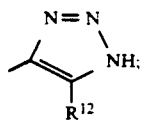

(p) CONHSO$_2$R$^{21}$;
(q) SO$_2$NHCOR$^{21}$;
(r) —SO$_2$NH-heteroaryl,
(s) —SO$_2$NHCONHR$^{21}$,
(t) —CH$_2$SO$_2$NH-heteroaryl,
(u) —CH$_2$SO$_2$NHCO—R$^{21}$,
(v) —CH$_2$CONH—SO$_2$R$^{21}$,
(w) —NHSO$_2$NHCO—R$^{21}$,
(x) —NHCONHSO$_2$—R$^{21}$,
wherein heteroaryl is an unsubstituted, monosubstituted or disubstituted five- or six-membered aromatic ring which can optionally contain 1 to 3 heteroatoms selected from the group consisting of O, N or S and wherein the substituents are members selected from the group consisting of
—OH, —SH, -C$_1$-C$_4$-alkyl, -C$_1$-C$_4$-alkoxy, halo(Cl, Br, F, I), —NO$_2$, —CO$_2$H, —CO$_2$-C$_1$-C$_4$-alkyl, —NH$_2$, —NH(C$_1$-C$_4$-alkyl) and —N(-C$_1$-C$_4$-alkyl)$_2$;

R$^{2a}$ and R$^{2b}$ are each independently
(a) H,
(b) halogen,
(c) NO$_2$,
(d) NH$_2$,
(e) C$_1$-C$_4$-alkylamino,
(f) di(C$_1$-C$_4$-alkyl)amino
(g) SO$_2$NHR$^9$,
(h) CF$_3$,
(i) C$_1$-C$_6$-alkyl, C$_2$-C$_6$-alkenyl, or C$_2$-C$_6$-alkynyl, or
(j) C$_1$-C$_4$-alkoxy;

R$^{3a}$ is
(a) H,
(b) halo (Cl, Br, I, F)
(c) C$_1$-C$_6$-alkyl,
(d) C$_1$-C$_6$-alkoxy,
(e) C$_1$-C$_6$-alkoxy-C$_1$-C$_4$-alkyl;

R$^{3b}$ is
(a) H,
(b) halo (Cl, Br, I, F)
(c) NO$_2$,
(d) C$_1$-C$_6$-alkyl, C$_2$-C$_6$-alkenyl, or C$_2$-C$_6$-alkynyl,
(e) C$_1$-C$_6$-acyloxy,
(f) C$_1$-C$_6$-cycloalkyl,
(g) C$_1$-C$_6$-alkoxy,
(h) —NHSO$_2$R$^4$,
(i) hydroxy C$_1$-C$_4$-alkyl,
(j) aryl-C$_1$-C$_4$-alkyl,
(k) C$_1$-C$_4$-alkylthio,
(l) C$_1$-C$_4$-alkylsulfinyl,
(m) C$_1$-C$_4$-alkylsulfonyl,
(n) NH$_2$,
(o) C$_1$-C$_4$-alkylamino,
(p) C$_1$-C$_4$-dialkylamino,
(q) perfluoro-C$_1$-C$_4$-alkyl,
(r) —SO$_2$—NHR$^9$,
(s) aryl or
(t) furyl;
wherein aryl is phenyl optionally substituted with one or two substituents selected from the group consisting of halo(Cl, Br, I, F) or C$_1$-C$_4$-alkyl, optionally substituted with members selected from the group consisting of N(R$^4$)$_2$, CO$_2$R$^4$, OH, N(R$^4$)CO$_2$R$^{21}$, S(O)$_x$R$^{21}$ wherein x is 0 to 2; C$_1$-C$_4$-alkoxy, NO$_2$, CF$_3$, C$_1$-C$_4$-alkylthio, OH, NH$_2$, —NH(C$_1$-C$_4$-alkyl), —N(C$_1$-C$_4$-alkyl)$_2$, —CO$_2$H, —CO$_2$-C$_1$-C$_4$-alkyl, N(R$^4$)CO$_2$R$^{21}$, or

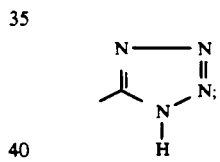

R$^4$ is H, straight chain or branched C$_1$-C$_6$-alkyl optionally substituted with aryl as defined above;
R$^{4a}$ is C$_1$-C$_6$-alkyl, aryl or aryl—CH$_2$— wherein aryl is as defined above;
R$^5$ is H,

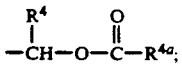

E is a single bond, —NR$^{13}$(CH$_2$)$_s$—, —S(O)$_x$(CH$_2$-)$_s$— where x is 0 to 2 and s is 0 to 5, —CH(OH)—, —O—, CO—;

R$^6$ is
(a) aryl as defined above;
(b) straight chain or branched C$_1$-C$_6$-alkyl, C$_2$-C$_5$-alkenyl or C$_2$-C$_5$-alkynyl each of which can be optionally substituted with a substituent selected from the group consisting of aryl as defined above, C$_3$-C$_7$-cycloalkyl, halo (Cl, Br, I, F) —OH, CF$_3$, —CF$_2$CF$_3$, CCl$_3$, —NH$_2$, —NH(-C$_1$-C$_4$-alkyl), —N(C$_1$-C$_4$-alkyl)$_2$, —NH—SO$_2$R$^4$, —COOR$^4$, —SO$_2$NHR$^9$, C$_1$-C$_4$-alkoxy, C$_1$-C$_4$-alkyl—S;
(c) an unsubstituted, monosubstituted or disubstituted heteroaromatic 5 or 6 membered cyclic ring which can contain one or two members selected from the group consisting of N, O, S, and wherein the substituents are members selected from the group consisting of —OH, —SH, $C_1$-$C_4$-alkyl, $C_1$-$C_4$-alkyloxy —$CF_3$, halo (Cl, Br, I, F), $NO_2$, —$CO_2H$, —$CO_2$-$C_1$-$C_4$-alkyl, —$NH_2$, —NH($C_1$-$C_4$-alkyl), —N($C_1$-$C_4$-alkyl)$_2$;

(d) $C_3$-$C_7$-cycloalkyl;

$R^7$ and $R^8$ are independently
(a) H,
(b) aryl-$C_1$-$C_4$-alkyl-,
(c) heteroaryl-$C_1$-$C_4$-alkyl-,
(d) $C_1$-$C_4$-alkyl optionally substituted with a substituent selected from the group consisting of —OH, —$NH_2$, guanidino, $C_1$-$C_4$-alkoxy, —S(O)$_x R^{21}$, $C_1$-$C_4$-alkylamino, $C_1$-$C_4$-dialkylamino, —$COOR^4$, —CON($R^4$)$R^{21}$, —O-CON($R^4$)$R^{21}$, —O—$COR^4$, $C_3$-$C_5$-cycloalkyl, —N($R^4$)CON($R^4$)$R^{21}$, —N($R^4$)$COOR^{21}$, —$CONHSO_2R^{21}$, —N($R^4$)$SO_2R^{21}$;
(e) $C_2$-$C_4$-alkenyl,
(f) —CO-aryl as defined above,
(g) $C_3$-$C_7$-cycloalkyl,
(h) halo (Cl, Br, I, F),
(i) —OH,
(j) —$OR^{21}$,
(k) perfluoro-$C_1$-$C_4$-alkyl,
(l) —SH,
(m) —S(O)$_x R^{21}$ where x is as defined above,
(n) —CHO,
(o) —$CO_2R^4$,
(p) —$SO_3H$,
(q) —N($R^4$)$_2$,
(r) —$NHCO_2R^{21}$,
(s) —$SO_2NR^9R^{10}$,
(t) —$CH_2OCOR^4$,
(u) —N($R^4$)—$SO_2$-$C_1$-$C_4$-alkyl,
(v) 5 or 6 membered saturated heterocycle containing one nitrogen atom and optionally containing one other heteroatom selected from N, O or S, such as pyrrolidine, morpholine, or piperazine,
(w) aryl as defined above,
(x) heteroaryl as defined above,
(y)

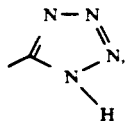

(z) —$NHSO_2$-perfluoro-$C_1$-$C_4$-alkyl,
(aa) —$CONHSO_2R^{21}$,
(bb) —$SO_2NHCOR^{21}$,
(cc) —$SO_2NH$-heteroaryl as defined above,
(dd) —S(O)$_x$-aryl as defined above,
(ee) —S(O)$_x CH_2$-aryl as defined above,
(ff) —CON($R^4$)$_2$;

$R^9$ is H, $C_1$-$C_5$-alkyl, phenyl or benzyl;
$R^{10}$ is H, $C_1$-$C_4$-alkyl;
$R^{11}$ is H, $C_1$-$C_6$-alkyl, $C_2$-$C_4$-alkenyl, $C_1$-$C_4$-alkoxy alkyl, or —$CH_2$—$C_6H_4R^{20}$;
$R^{12}$ is —CN, —$NO_2$ or —$CO_2R^4$;
$R^{13}$ is H, $C_1$-$C_4$-acyl, $C_1$-$C_6$-alkyl, allyl, $C_3$-$C_6$-cycloalkyl, phenyl or benzyl;
$R^{14}$ is H, $C_1$-$C_8$-alkyl, $C_1$-$C_8$-perfluoroalkyl, $C_3$-$C_6$-cycloalkyl, phenyl or benzyl;
$R^{15}$ is H, $C_1$-$C_6$-alkyl;

$R^{16}$ is H, $C_1$-$C_6$-alkyl, $C_3$-$C_6$-cycloalkyl, phenyl or benzyl;
$R^{17}$ is —$NR^9R^{10}$, —$OR^{10}$, —$NHCONH_2$, —$NHCSNH_2$,

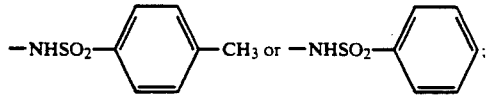

$R^{18}$ and $R^{19}$ are independently $C_1$-$C_4$-alkyl or taken together are —(CH$_2$)$_q$— where q is 2 or 3;
$R^{20}$ is H, —$NO_2$, —$NH_2$, —OH or —$OCH_3$;
$R^{21}$ is
(a) aryl as defined above;
(b) heteroaryl as defined above;
(c) $C_1$-$C_6$-alkyl optionally substituted with a substituent selected from the group consisting of aryl as defined above, heteroaryl as defined above, —OH, —$NH_2$, —NH($C_1$-$C_4$-alkyl), —N($C_1$-$C_4$-alkyl)$_2$, —$CO_2H$, —$CO_2R^4$, halo (Cl, Br, F, I), —$CF_3$;
(d) $C_3$-$C_5$-cycloalkyl;

X is
(a) a carbon-carbon single bond,
(b) —CO—,
(c) —O—,
(d) —S—,
(e)

(f)

(g)

(h) —$OCH_2$—,
(i) —$CH_2O$—
(j) —$SCH_2$—,
(k) —$CH_2S$—,
(l) —NHC($R^9$)($R^{10}$),
(m) —$NR^9SO_2$—,
(n) —$SO_2NR^9$—,
(o) —C($R^9$)($R^{10}$)NH—,
(p) —CH=CH—,
(q) —CF=CF—,
(r) —CH=CF—,
(s) —CF=CH—,
(t) —$CH_2CH_2$—,
(u) —$CF_2CF_2$—,
(v)

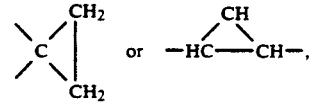

(w)

(x)

(y)

or (z)

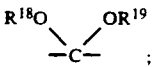

r is 1 or 2; and
the pharmaceutically acceptable salts thereof.

One embodiment of the compounds of formula (I) are those compounds
wherein:
J is —C(=M)—;
K is

b is a double bond;
$R^1$ is
(a) —COOH,
(b)

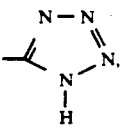

(c)

(d) —NH—SO$_2$CF$_3$,
(e) —CO$_2$R$^4$,
(f) CONHSO$_2$R$^{21}$;
(g) SO$_2$NHCOR$^{21}$;
(h) —SO$_2$NH-heteroaryl,
(i) —SO$_2$NHCONHR$^{21}$,
(j) —CH$_2$SO$_2$NH-heteroaryl,
(k) —CH$_2$SO$_2$NHCO—R$^{21}$
(l) —CH$_2$CONH—SO$_2$R$^{21}$,
(m) —NHSO$_2$NHCO—R$^{21}$,
(n) —NHCONHSO$_2$—R$^{21}$,
$R^{2a}$ and $R^{2b}$ are H, F, Cl, CF$_3$ or C$_1$-C$_6$-alkyl;
$R^{3a}$ is H;

$R^{3b}$ is H, F, Cl, CF$_3$, C$_1$-C$_6$-alkyl, C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$ or —NH—SO$_2$CH$_3$;
E is a single bond, —O— or —S—;
$R^6$ is
 (a) C$_1$-C$_5$-alkyl optionally substituted with a substituent selected from the group consisting of Cl, CF$_3$, CCl$_3$, —O—CH$_3$, —OC$_2$H$_5$, —S—CH$_3$, —S—C$_2$H$_5$ or phenyl;
 (b) C$_2$-C$_5$-alkenyl or C$_2$-C$_5$-alkynyl;
$R^7$ and $R^8$ are independently
 (a) H,
 (b) C$_1$-C$_4$-alkyl,
 (c) C$_2$-C$_4$-alkenyl,
 (d) —OH,
 (e) —CH$_2$OCOR$^4$,
 (f) —NH$_2$,
 (g)

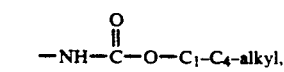

(h) -C$_1$-C$_4$-alkoxy,
 (i) —NH(C$_1$-C$_4$-alkyl)$_2$,
 (j) —N(C$_1$-C$_4$-alkyl)$_2$,
 (k) halo(Cl, F, Br),
 (l) —CF$_3$,
 (m) —CO$_2$R$^4$,
 (n) —CH$_2$—OH,
 (o) 5 or 6 membered saturated heterocycle containing one nitrogen atom and optionally containing one other heteroatom selected from N, O, or S, such as pyrrolidine, morpholine, or piperazine;
 (p) —CO-aryl as defined above,
 (q) —S(O)$_x$—C$_1$-C$_4$-alkyl;
 (r) —SO$_2$—NH—C$_1$-C$_4$-alkyl,
 (s) —SO$_2$—NH-aryl as defined above,
 (t) —NH—SO$_2$CH$_3$,
 (u) aryl as defined above;
 (v) heteroaryl as defined above;
 (w)

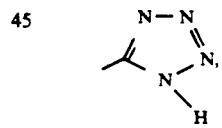

X is a C—C single bond or —CO—; and,
r is one.

In a class of this embodiment are those compounds wherein:
E is a single bond or —S—;
r is one,
$R^{2a}$, $R^{2b}$, $R^{3a}$ and $R^{3b}$ are each H;
$R^6$ is n-propyl, n-butyl, —CH$_3$, —CH$_2$CH$_3$, or —CH$_2$—S—CH$_3$;
$R^7$ is —NHSO$_2$CF$_3$, —CH$_2$OH, —CH$_2$OCOR$^4$, —CO$_2$R$^4$, —N(CH$_3$)$_2$,

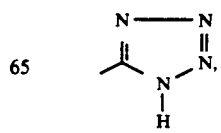

—NHCO$_2$—C$_1$-C$_4$-alkyl, H, —C$_1$-C$_4$-alkyl, aryl, or a 5 or 6 membered saturated heterocycle as defined above;
R$^8$ is H, —C$_1$-C$_4$-alkyl, aryl, heteroaryl, Cl, F, CF$_3$;
R$^1$ is
(a) —COOH,
(b)

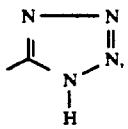

(c)

(d) —NH—SO$_2$—CF$_3$,
(e) CONHSO$_2$R$^{21}$;
(f) SO$_2$NHCOR$^{21}$;
(g) —SO$_2$NH-heteroaryl,
(h) —SO$_2$NHCONHR$^{21}$,
(i) —CH$_2$SO$_2$NH-heteroaryl,
(j) —CH$_2$SO$_2$NHCO—R$^{21}$,
(k) —CH$_2$CONH—SOR$^{21}$,
(l) —NHSO$_2$NHCO—R$^{21}$,
(m) —NHCONHSO$_2$—R$^{21}$, X is a single bond.

In naming compounds of Formula (I) which contain a biphenylmethyl substituent, it should be noted that the following two names for compound (i) shown below are considered to be equivalent:

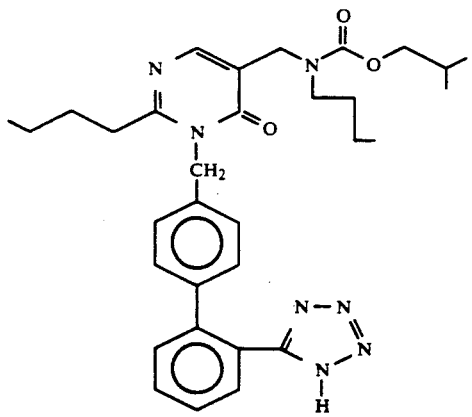

(1) 2-n-Butyl-5-(N-n-butyl-N-isobutyloxycarbonylamino)methyl-3-(2'-(tetrazol-5-yl)biphen-4-yl)methylpyrimidin-4(3H)-one; or,
(2) 2-n-Butyl-5-(N-n-butyl-N-isobutyloxycarbonylamino)methyl-3-[(2'-(tetrazol-5-yl)[1,1]-biphenyl-4-yl)methyl]pyrimidin-4(3H)-one.

Exemplifying the foregoing class are the following compounds:

(1) 2-n-Butyl-1-(2'-(tetrazol-5-yl)biphen-4-yl)methylpyrimidin-4(1H)-one;
(2) 2-n-Butyl-1-(2'-(tetrazol-5-yl)biphen-4-yl)methyl-5,6-dimethylpyrimidin-4(1H)-one;
(3) 2-n-Butyl-1-(2'-(tetrazol-5-yl)biphen-4-yl)methyl-6-hydroxymethyl-5-phenylpyrimidin-4(1H)-one;
(4) 2-n-Butyl-1-(2'-(tetrazol-5-yl)biphen-4-yl)methyl-5-(2-chloro)phenyl-6-hydroxymethylpyrimidin-4(1H)-one;
(5) 2-n-Butyl-1-(2'-(tetrazol-5-yl)biphen-4-yl)methyl-5-chloro-6-hydroxymethylpyrimidin-4(1H)-one;
(6) 2-n-Butyl-1-(2'-(tetrazol-5-yl)biphen-4-yl)methyl-6-carboethoxypyrimidin-4(1H)-one;
(7) 2-n-Butyl-1-(2'-(tetrazol-5-yl)biphen-4-yl)methyl-6-carboethoxy-5-(2-chloro)phenylpyrimidin-4(1H)-one;
(8) 2-n-Butyl-1-(2'-(tetrazol-5-yl)biphen-4-yl)methyl-5-(2,5-dichloro)phenyl-6-hydroxymethylpyrimidin-4(1H)-one;
(9) 2-n-Butyl-1-(2'-(tetrazol-5-yl)biphen-4-yl)methyl-6-acetoxymethyl-5-(2-chloro)phenylpyrimidin-4(1H)-one;
(10) 2-n-Butyl-1-(2'-(tetrazol-5-yl)biphen-4-yl)methyl-5-(2-carboethoxy)phenylpyrimidin-4(1H)-one;
(11) 2-n-Butyl-1-(2'-(tetrazol-5-yl)biphen-4-yl)methyl-5-(2-carboethoxy)phenyl-6-methylpyrimidin-4(1H)-one;
(12) 2-n-Butyl-1-(2'-(tetrazol-5-yl)biphen-4-yl)methyl-5-(2-carboxy)phenyl-6-methylpyrimidin-4(1H)-one;
(13) 2-n-Butyl-1-(2'-(tetrazol-5-yl)biphen-4-yl)methyl-5-(2-carboxy)phenyl-6-dimethylaminopyrimidin-4(1H)-one;
(14) 2-n-Butyl-1-(2'-(carboxy)biphen-4-yl)methylpyrimidin-4(1H)-one;
(15) 2-n-Butyl-1-(2'-(carboxy)biphen-4-yl)methyl-6-(tetrazol-5-yl)pyrimidin-4(1H)-one;
(16) 2-n-Butyl-1-(2'-(carboxy)biphen-4-yl)methyl-5-methyl-6-(tetrazol-5-yl)pyrimidin-4(1H)-one;
(17) 2-n-Butyl-1-(2'-(carboxybiphen-4-yl)methyl)-5-(2-chloro)phenyl-6-(tetrazol-5-yl)pyrimidin-4(1H)-one;
(18) 2-n-Butyl-1-(2'-(tetrazol-5-yl)biphen-4-yl)methyl-5-(2-chloro)phenyl-6-(tetrazol-5-yl)pyrimidin-4(1H)-one;
(19) 2-Butyl-6-carboxy-5-(2-chloro)phenyl-1-(2'-(N-(1,3-5-triazin-2-yl)sulfamido)biphen-4-yl)methylpyrimidin-4(1H)-one;
(20) 2-Butyl-6-carbomethoxy-5-(2-chloro)phenyl-1-(2'-(N-1,3,5-triazin-2-yl)sulfamido)biphen-4-yl)methylpyrimidin-4(1H)-one;
(21) 2-Butyl-6-carboxy-5-(2-chloro)phenyl-1-(2'-(N-(pyrimidin-2-yl)sulfamido)biphen-4-yl)methylpyrimidin-4(1H)-one;
(22) 1-(2'-(N-Acetylsulfamido)biphen-4-yl)methyl-2-butyl-6-carboxy-5-(2-chloro)phenylpyrimidin-4(1H)-one;
(23) 1-(2'-(N-Benzoylsulfamido)biphen-4-yl)methyl-2-butyl-6-carboxy-5-(2-chloro)phenylpyrimidin-4(1H)-one;
(24) 2-Butyl-6-carboxy-5-(2-chloro)phenyl-1-(2'-(N-trifluoracetylsulfamido)biphen-4-yl)methylpyrimidin-4(1H)-one;
(25) 2-Butyl-6-carboxy-5-(2-chloro)phenyl-1-(2'-((N-methylsulfonyl)carboxamido)biphen-4-yl)methylpyrimidin-4(1H)-one;
(26) 2-Butyl-6-carboxy-5-(2-chloro)phenyl-1-(2'-((N-phenylsulfonyl)carboxamido)biphen-4-yl)methylpyrimidin-4(1H)-one;
(27) 2-Butyl-6-carboxy-5-(2-chloro)phenyl-1-(2'-((N-morpholin-4-phenylsulfonyl)carboxamido)biphen-4-yl)methylpyrimidin-4(1H)-one;

(28) 2-Butyl-6-carboxy-5-(2-chloro)phenyl-1-(2'-((N-(dimethylamino)sulfonyl)carboxamido)biphen-4-yl)methylpyrimidin-4(1H)-one; and,

(29) 6-Carboxy-2-cyclopropyl-5-(2-chloro)phenyl-1-(2'(tetrazol-5-yl)biphen-4-yl)methylpyrimidin-4(1H)-one.

In a second embodiment are those compounds of formula (I) wherein:

K is —C(=O)—;
J is

a is a double bond;
$R^1$ is
- (a) —COOH,
- (b)

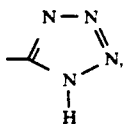

- (c)

- (d) —NH—$SO_2CF_3$,
- (e) $CO_2R^4$,
- (f) $CONHSO_2R^{21}$;
- (g) $SO_2NHCOR^{21}$;
- (h) —$SO_2$NH-heteroaryl,
- (i) —$SO_2$NHCONH$R^{21}$,
- (j) —$CH_2SO_2$NH-heteroaryl,
- (k) —$CH_2SO_2$NHCO—$R^{21}$,
- (l) —$CH_2$CONH—$SO_2R^{21}$,
- (m) —NH$SO_2$NHCO—$R^{21}$,
- (n) —NHCONH$SO_2$—$R^{21}$, $R^{2a}$ and $R^{2b}$ are H, F, Cl, $CF_3$, $C_1$-$C_6$-alkyl, $C_2$-$C_6$-alkenyl, $C_2$-$C_6$-alkynyl;

$R^{3a}$ is H, F or Cl;

$R^{3b}$ is H, F, Cl, $CF_3$, $C_1$-$C_6$-alkyl, $C_2$-$C_6$-alkenyl, $C_2$-$C_6$-alkynyl, $C_5$-$C_6$-cycloalkyl, —$COOCH_3$, —$COOC_2H_5$, —$SO_2$—$CH_3$, —$N(R^4)_2$ or —NH—$SO_2CH_3$;

E is a single bond, —O— or —S—;

$R^6$ is
- (a) $C_1$-$C_5$-alkyl optionally substituted with a substituent selected from the group consisting of Cl, $CF_3$, $CCl_3$, —O—$CH_3$, —$OC_2H_5$, —S—$CH_3$, —S—$C_2H_5$ or phenyl;
- (b) $C_2$-$C_5$-alkenyl or $C_2$-$C_5$-alkynyl;
- (c) $C_3$-$C_5$-cycloalkyl;

$R^7$ and $R^8$ are independently
- (a) H,
- (b) $C_1$-$C_4$-alkyl optionally substituted with —$N(R^4)CO_2R^{21}$, —$S(O)_xR^{21}$, aryl, —$N(R^4)_2$, —$CO_2R^4$, —$N(R^4)CON(R^4)R^{21}$, —$CON(R^4)R^{21}$,
- (c) $C_2$-$C_4$-alkenyl,

- (d) —OH,
- (e) —$CH_2OCOR^4$,
- (f) —$NH_2$,
- (g) —$N(R^4)COOR^{21}$,
- (h) —$C_1$-$C_4$-alkoxy,
- (i) —NH($C_1$-$C_4$-alkyl),
- (j) —N($C_1$-$C_4$-alkyl)$_2$,
- (k) halo(Cl, F, Br),
- (l) —$CF_3$,
- (m) —$CO_2R^4$,
- (n) —$CH_2$—OH,
- (o) 5 or 6 membered saturated heterocycle as defined above,
- (p) —CO-aryl as defined above,
- (q) —$S(O)_x$—$C_1$-$C_4$-alkyl
- (r) —$SO_2$—NH—$C_1$-$C_4$-alkyl,
- (s) —$SO_2$—NH-aryl as defined above,
- (t) —NH—$SO_2CH_3$,
- (u) aryl as defined above;
- (v) heteroaryl as defined above;
- (w)

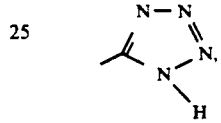

X is a C—C single bond or —CO—; and,
r is one.

In a class of this embodiment are those compounds of formula (I) wherein:

E is a single bond or —S—;
r is one,
$R^1$ is
- (a) —$CO^2R^4$
- (b) —$CONHSO_2R^{21}$,
- (c) —$NHSO_2CF_3$,
- (d) —$SO_2NHCOR^{21}$,
- (e) —$SO_2$NH-heteroaryl,
- (f)

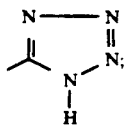

$R^{2a}$ and $R^{2b}$ are H, F, Cl, $CF_3$, $C_1$-$C_6$-alkyl, $C_2$-$C_6$-alkenyl, $C_2$-$C_6$-alkynyl;

$R^{3a}$ is H, F, or Cl;

$R^{3b}$ is H, F, Cl, $CF_3$, $C_1$-$C_6$-alkyl, $C_2$-$C_6$-alkenyl, $C_2$-$C_6$-alkynyl, $C_5$-$C_6$-cycloalkyl, —$COOCH_3$, —$COOC_2H_5$, —$SO_2$—$CH_3$, —$N(R^4)_2$ or —NH—$SO_2CH_3$;

$R^6$ is n-propyl, n-butyl, —$CH_2CH_3$, cyclopropyl or cyclopropylmethyl

X is a single.

Exemplifying this class are the following compounds:

(1) 2-n-Butyl-3-(2'-(tetrazol-5-yl)biphen-4-yl)methylpyrimidin-4(3H)-one;

(2) 2-n-Butyl-3-(2'-(tetrazol-5-yl)biphen-4-yl)methyl-5,6-dimethylpyrimidin-4(3H)-one;

(3) 2-n-Butyl-3-(2'-(tetrazol-5-yl)biphen-4-yl)methyl-5-ethoxycarbonyl-6-phenylpyrimidin-4(3H)-one;

(4) 2-n-Butyl-3-(2'-(tetrazol-5-yl)biphen-4-yl)methyl-5-ethoxycarbonyl-6-ethylpyrimidin-4(3H)-one;
(5) 2-n-Butyl-3-(2'-(tetrazol-5-yl)biphen-4-yl)methyl-6-(2-chloro)phenyl-5-hydroxymethylpyrimidin-4(3H)-one;
(6) 2-n-Butyl-3-(2'-(tetrazol-5-yl)biphen-4-yl)methyl-6-chloro-5-hydroxymethylpyrimidin-4(3H)-one;
(7) 2-n-Butyl-3-(2'-(tetrazol-5-yl)biphen-4-yl)methyl-6-dimethylamino-5-hydroxymethylpyrimidin-4(3H)-one;
(8) 2-n-Butyl-3-(2'-(tetrazol-5-yl)biphen-4-yl)methyl-6-dimethylamino-5-ethylpyrimidin-4(3H)-one;
(9) 2-n-Butyl-3-(2'-(tetrazol-5-yl)biphen-4-yl)methyl-6-acetoxymethyl-5-(2-chloro)phenylpyrimidin-4(3H)-one;
(10) 2-n-Butyl-3-(2'-(tetrazol-5-yl)biphen-4-yl)methyl-6-ethyl-5-phenylpyrimidin-4(3H)-one;
(11) 2-n-Butyl-3-(2'-(tetrazol-5-yl)biphen-4-yl)methyl-5-ethyl-6-(2-chloro)phenylpyrimidin-4(3H)-one;
(12) 2-n-Butyl-3-(2'-(tetrazol-5-yl)biphen-4-yl)methyl-5-(2-carboxy)phenyl-6-ethylpyrimidin-4(3H)-one;
(13) 2-n-Butyl-3-(2'-(tetrazol-5-yl)biphen-4-yl)methyl-5-(2-carboethoxyphenyl)-6-ethylpyrimidin-4(3H)-one;
(14) 2-n-Butyl-3-(2'-(carboxy)biphen-4-yl)methyl-5-(2-(tetrazol-5-yl))phenyl-6-ethylpyrimidin-4(3H)-one;
(15) 2-n-Butyl-3-(2'-(tetrazol-5-yl)biphen-4-yl)methyl-5-[2-(tetrazol-5-yl)]phenyl-6-ethylpyrimidin-4(3H)-one;
(16) 2-n-Butyl-3-(2'-(tetrazol-5-yl)biphen-4-yl)methyl-5-(tetrazol-5-yl)-6-ethylpyrimidin-4(3H)-one;
(17) 2-n-Butyl-3-(2'-carboxybiphen-4-yl)methyl-5-(tetrazol-5-yl)-6-ethylpyrimidin-4(3H)-one;
(18) 2-Butyl-5-(2-chloro)phenyl-6-methyl-3-(2'-(N-(phenylsulfonyl)carboxamido)biphen-4-yl)methylpyrimidin-4(3H)-one;
(19) 2-Butyl-5-(2-chloro)phenyl-6-methyl-3-(2'-(N-(methylsulfonyl)carboxamido)biphen-4-yl)methylpyrimidin-4(3H)-one;
(20) 2-Butyl-5-(2-chloro)phenyl-6-methyl-3-(2'-(N-(trifluoromethylsulfonyl)carboxamido)biphen-4-yl)methylpyrimidin-4(3H)-one;
(21) 2-Butyl-5-(2-chloro)phenyl-6-methyl-3-(2'-(N-(morpholin-4-yl)sulfonylcarboxamido)biphen-4-yl)methylpyrimidin-4(3H)-one;
(22) 3-(2'-(N-Acetylsulfamido)biphen-4-yl)methyl-2-butyl-5-(2-chloro)phenyl-6-methylpyrimidin-4(3H)-one;
(23) 3-(2'-(N-Benzoylsulfamido)biphen-4-yl)methyl-2-butyl-5-(2-chloro)phenyl-6-methylpyrimidin-4(3H)-one;
(24) 2-Butyl-5-(2-chloro)phenyl-6-methyl-3-(2'-(N-trifluoroacetylsulfamido)biphen-4-yl)methylpyrimidin-4(3H)-one;
(25) 2-Butyl-5-(2-chloro)phenyl-6-methyl-3-(2'-(N-(pyrimidin-2-yl)sulfamido)biphen-4-yl)methylpyrimidin-4(3H)-one;
(26) 2-Butyl-5-(2-chloro)phenyl-6-methyl-3-(2'-(N-(1,3-5-triazin-2-yl)sulfamido)biphen-4-yl)methylpyrimidin-4(3H)-one;
(27) 2-Butyl-5-(2-chloro)phenyl-6-methyl-3-(2'-(N-(1,2,4-oxadiazol-3-yl)sulfamido)biphen-4-yl)methylpyrimidin-4(3H)-one;
(28) 3-(5'-allyl-2'-(tetrazol-5-yl)biphen-4-yl)methyl-2-butyl-5-(2-chloro)phenyl-6-methylpyrimidin-4(3H)-one;
(29) 2-Butyl-5-(2-chloro)phenyl-6-methyl-3-(5'-propyl-2'-(tetrazol-5-yl)biphen-4-yl)methylpyrimidin-4(3H)-one;
(30) 5-(2-Chloro)phenyl-2-cyclopropyl-6-methyl-3-(5'-propyl-2'-(tetrazol-5-yl)biphen-4-yl)methylpyrimidin-4(3H)-one;
(31) 2-Butyl-3-(4'-chloro-2'-(tetrazol-5-yl)biphen-4-yl)methyl-5-(2-chloro)phenyl-6-methylpyrimidin-4(3H)-one;
(32) 2-Butyl-5-(2-chloro)phenyl-6-methyl-3-(5'-phenyl-2'-(tetrazol-5-yl)biphen-4-yl)methylpyrimidin-4(3H)-one;
(33) 2-Butyl-5-(2-chloro)phenyl-6-methyl-3-(5'-(4-methyl)phenyl-2'-(tetrazol-5-yl)biphen-4-yl)methylpyrimidin-4(3H)-one;
(34) 5-(2-Chloro)phenyl-2-cyclopropyl-6-methyl-3-(5'-(4-methyl)phenyl-2'-(tetrazol-5-yl)biphen-4-yl)methylpyrimidin-4(3H)-one;
(35) 5-(2-Chloro)phenyl-2-cyclopropyl-6-methyl-3-(5'-propyl-2'-((N-benzoyl)sulfonamido)biphen-4-yl)methylpyrimidin-4(3H)-one;
(36) 2-n-Butyl-5-(N-n-butyl-N-isobutyloxycarbonylamino)methyl-6-methyl-3-(2'-tetrazol-5-yl)biphen-4-yl)methylpyrimidin-4(3H)-one;
(37) 2-n-Butyl-5-[2-(N-n-butyl-N-isobutyloxycarbonylamino)]ethyl-6-methyl-3-(2'-tetrazol-5-yl)biphen-4-yl)methylpyrimidin-4(3H)-one;
(38) 2-n-Butyl-6-(N-n-butyl-N-isobutyloxycarbonylamino)methyl-3-(2'-tetrazol-5-yl)biphen-4-yl)methylpyrimidin-4(3H)-one;
(39) 2-n-Butyl-6-methyl-5-(3-phenyl)propyl-3-(2'-tetrazol-5-yl)biphen-4-yl)methylpyrimidin-4(3H)-one;
(40) 2-n-Butyl-5-(N-benzyl-N-isobutyloxycarbonylamino)methyl-6-methyl-3-(2'-tetrazol-5-yl)biphen-4-yl)methylpyrimidin-4(3H)-one;
(41) 5-(N-Benzyl-N-isobutyloxycarbonylamino)methyl-6-methyl-2-n-propyl-3-(2'-tetrazol-5-yl)biphen-4-yl)methylpyrimidin-4(3H)-one;
(42) 5-(N-n-Butyl-N-isobutyloxycarbonylamino)methyl-6-methyl-2-n-propyl-3-(2'-tetrazol-5-yl)biphen-4-yl)methylpyrimidin-4(3H)-one;
(43) 5-(N-n-Butyl-N-butanoylamino)methyl-6-methyl-2-n-propyl-3-(2'-tetrazol-5-yl)biphen-4-yl)methylpyrimidin-4(3H)-one;
(44) 5-(N-Benzyl-N-isobutyloxycarbonyl)amino-6-methyl-2-n-butyl-3-(2'-tetrazol-5-yl)biphen-4-yl)methylpyrimidin-4(3H)-one;
(45) 3-(2'-(N-Benzoylsulfonamido)biphen-4-yl)methyl-5-(N-n-butyl-N-isobutyloxycarbonylamino)methyl-6-methyl-2-n-propyl-pyrimidin-4(3H)-one;
(46) 2-n-Butyl-5-(N,N-di-n-butylcarboxamido)methyl-6-methyl-3-(2'-tetrazol-5-yl)biphen-4-yl)methyl-pyrimidin-4(3H)-one;
(47) 2-n-Butyl-5-(N,N-di-n-butylcarboxamido)methyl-6-methyl-3-(2'-tetrazol-5-yl)biphen-4-yl)pyrimidin-4(3H)-one; and,
(48) 2-n-Butyl-6-(N,N-di-n-butylcarboxamido)methyl-5-methyl-3-(2'-tetrazol-5-yl)biphen-4-yl)pyrimidin-4(3H)-one.

In a third embodiment are those compounds of formula (I)
wherein:
K is $-C(=NR^{21})$;
J is $-\overset{R^7}{\underset{}{C}}=$;

a is a double bond;

$R^1$ is
(a) —COOH,
(b)

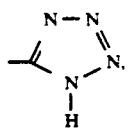

(c)

$$-\underset{\underset{OR^4}{|}}{\overset{\overset{O}{\|}}{P}}-R^9;$$

(d) —NH—SO$_2$CF$_3$,
(e) CO$_2$R$^4$,
(f) CONHSO$_2$R$^{21}$;
(g) SO$_2$NHCOR$^{21}$;
(h) —SO$_2$NH-heteroaryl,
(i) —SO$_2$NHCONHR$^{21}$,
(j) —CH$_2$SO$_2$NH-heteroaryl,
(k) —CH$_2$SO$_2$NHCO—R$^{21}$,
(l) —CH$_2$CONH—SO$_2$R$^{21}$,
(m) —NHSO$_2$NHCO—R$^{21}$,
(n) —NHCONHSO$_2$—R$^{21}$, $R^{2a}$ and $R^{2b}$ are H, F, Cl, CF$_3$ C$_1$-C$_6$-alkyl, C$_2$-C$_6$-alkenyl, C$_2$-C$_6$-alkynyl;

$R^{3a}$ is H, F or Cl;

$R^{3b}$ is H, F, Cl, CF$_3$, C$_1$-C$_6$alkyl, C$_2$-C$_6$-alkenyl, C$_2$-C$_6$-alkynyl, C$_5$-C$_6$ cycloalkyl, —COOCH$_3$, —COOC$_2$H$_5$, —SO$_2$—CH$_3$, NH$_2$, —N(C$_1$-C$_4$-alkyl)$_2$ —NH—SO$_2$CH$_3$, E is a single bond, —O— or —S—;

$R^6$ is (a) C$_1$-C$_5$-alkyl optionally substituted with a substituent selected from the group consisting of Cl, CF$_3$, CCl$_3$, —O—CH$_3$, —OC$_2$H$_5$, —S—CH$_3$, —S—C$_2$H$_5$ or phenyl;
(b) C$_2$-C$_5$-alkenyl or C$_2$-C$_5$-alkynyl;

$R^7$ and $R^8$ are independently
(a) H,
(b) C$_1$-C$_6$-alkyl,
(c) C$_2$-C$_6$-alkenyl,
(d) —OH,
(e) —CH$_2$OCOR$^4$,
(f) —NH$_2$,
(g)

(h) -C$_1$-C$_4$-alkoxy,
(i) —NH(C$_1$-C$_4$-alkyl),
(j) —N(C$_1$-C$_4$-alkyl)$_2$,
(k) halo(Cl, F, Br),
(l) —CF$_3$,
(m) —CO$_2$R$^4$,
(n) —CH$_2$—OH,
(o) 5 or 6 membered saturated heterocycle as defined above,
(p) —CO-aryl as defined above,
(q) —S(O)$_x$-C$_1$-C$_4$-alkyl
(r) —SO$_2$—NH-C$_1$-C$_4$-alkyl,
(s) —SO$_2$—NH-aryl as defined above,
(t) —NH—SO$_2$CH$_3$,
(u) aryl as defined above;
(v) heteroaryl as defined above;
(w)

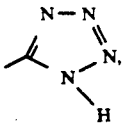

X is a C—C single bond or —CO—; and,
r is one.

In a class of this embodiment are those compounds of formula (I)
wherein:
E is a single bond or —S—;
r is one,
$R^{2a}$, $R^{2b}$, $R^{3a}$ and $R^{3b}$ are each H;
$R^6$ is n-propyl, n-butyl, —CH$_3$, or —CH$_2$CH$_3$;
$R^7$ and $R^8$ are independently selected from: H, C$_1$-C$_6$-alkyl, —Cl, C$_1$-C$_4$-alkoxy, —F, —CH$_2$OH, NO$_2$, —CO$_2$R$^4$ —NH—COO-C$_1$-C$_4$-alkyl, —CF$_3$, —CH$_2$OCOR$^4$, —NH$_2$, —NH(C$_1$-C$_4$-alkyl), —N(-C$_1$-C$_4$-alkyl)$_2$,

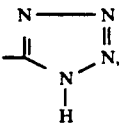

aryl or a 5 or 6 membered saturated heterocycle as defined above;
X is a single bond or —CO—.

Exemplifying this class are the following compounds:

(1) N-Methyl 2-butyl-5-(2-chloro)phenyl-6-methyl-3-(2'-(tetrazol-5-yl)biphen-4-yl)methylpyrimidin-4(3H)-imine;

(2) N-Ethyl 2-butyl-5-(2-chloro)phenyl-6-methyl-3-(5'-propyl-2'-(tetrazol-5-yl)biphen-4-yl)methylpyrimidin-4(3H)-imine;

(3) N-Propyl 2-cyclopropyl-6-methyl-3(2'-(tetrazol-5-yl)biphen-4-yl)methyl-5-(2-trifluoromethyl) phenylpyrimidin-4(3H)-imine;

(4) N-Phenyl 2-butyl-5-(2-chloro)phenyl-6-methyl-3-(2'-(tetrazol-5-yl)biphen-4-yl)methyl-pyrimidin-4(3H)-imine;

(5) N-Benzyl 2-butyl-5(2-chloro)phenyl-6-methyl-3(2'-(tetrazol-5-yl)biphen-4-yl)methylpyrimidin-4(3H)-imine;

(6) N-Carboxymethyl 2-butyl-5-(2-chloro)phenyl-6-methyl-3(2'-(tetrazol-5-yl)biphen-4-yl)methylpyrimidin-4(3H)-imine;

(7) N-(Pyridin-2-yl) 5-(2-chloro)phenyl-2-cyclopropyl-6-methyl-3-(5'-(4-methyl)phenyl-2'-(tetrazol-5-yl)biphen-4-yl)methylpyrimidin-4(3H)-imine; and, (8) N-Cyclopropyl 3-(2'-((N-benzoyl)sulfonamido)biphen-4-yl)methyl-2-butyl-5-(2-chloro)phenyl-6-methylpyrimidin-4(3H)-imine.

| TABLE OF ABBREVIATIONS USED | |
|---|---|
| Reagents: | |
| NBS | N-bromosuccinimide |

TABLE OF ABBREVIATIONS USED

| | |
|---|---|
| AIBN | Azo(bis)isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO$_2$CF$_3$ |
| OTs | OSO$_2$-(4-methyl)phenyl |
| OMs | OSO$_2$C$_3$ |
| Ph | phenyl |
| FAB-MS (FABMS) | Fast atom bombardment mass spectroscopy |
| NOE | Nuclear Overhauser Effect |
| SiO$_2$ | silica gel |
| trityl | triphenylmethyl |

Pyrimidinones (wherein J is —C(O)—) substituted in the 1,2,5, and 6-positions may be synthesized as shown in Scheme 1. Amidines with an R$^6$ substituent may be reacted with a β-carbonyl ester to give a 4-hydroxypyrimidine. Conversion of the hydroxy group to a chloride and then to an amine can be achieved by first treating the 4-hydroxypyrimidine with POCl$_3$ and then with ammonia.[1] Reaction of the 4-aminopyrimidine with the appropriate alkyl halide followed by treatment with aqueous hydroxide gives the 1,4-dihydro-4-oxopyrimidine 3.[2]

Processes and methods for preparing the compounds of the invention are illustrated in the following reaction Schemes.

SCHEME 1

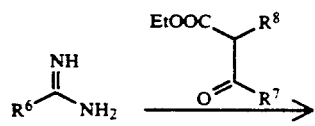

SCHEME 1 (continued)

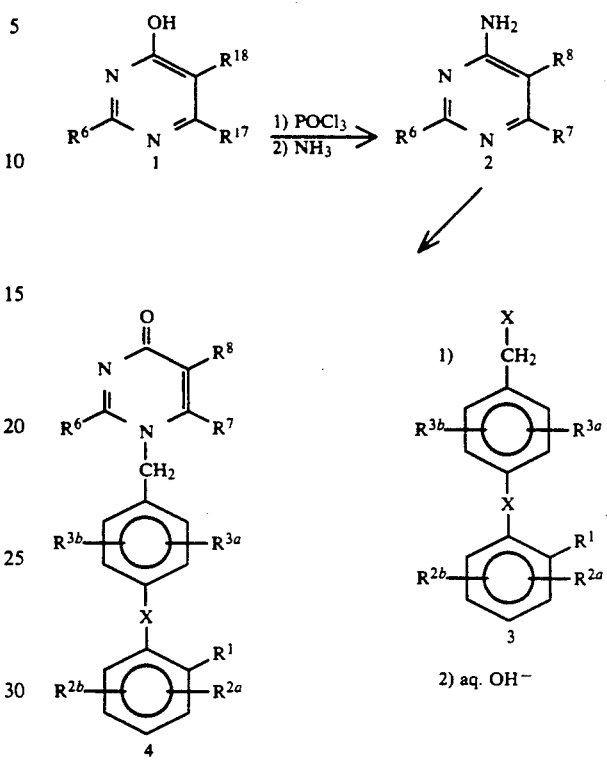

The benzyl halides 3 including the more preferred alkylating agents (9a, 9b and 9c, Scheme 2) can be prepared as described in European Patent Applications 253,310 and 291,969 and the references cited therein. However, a preferred method to prepare the biphenyl precursors 8a, 8b and 8c using Ni (O) or Pd (O) catalyzed cross-coupling reaction [E. Negishi, T. Takahashi, and A. O. King, Org. Synthesis, 66, 67 (1987)] is outlined in Reaction Scheme 2. As shown in Reaction Scheme 2, treatment of 4-bromo toluene (4) with t-BuLi, followed by the addition of a solution of ZnCl$_2$, produces the organo-zinc compound (6). Compound (6) is then coupled with 7a or 7b in the presence of Ni(PPh$_3$)Cl$_2$ catalyst to produce the desired biphenyl compound 8a and 8b (PPh$_3$=triphenylphosphine). Similarily, 1-iodo-2-nitro-benzene (7c) is coupled with organo-zinc compound 6 in the presence of Pd(PPh$_3$)$_4$ catalyst [prepared by treating Cl$_2$Pd(PPh$_3$)$_2$ with (i-Bu)$_2$AlH (2 equiv.)] to give the biphenyl compound 8c. These precursors, 8a, 8b and 8c, are then transformed into halomethylbiphenyl derivatives 9a, 9b and 9c, respectively, according to procedures described in European Patent Applications 253,310 and 291,969.

SCHEME 2

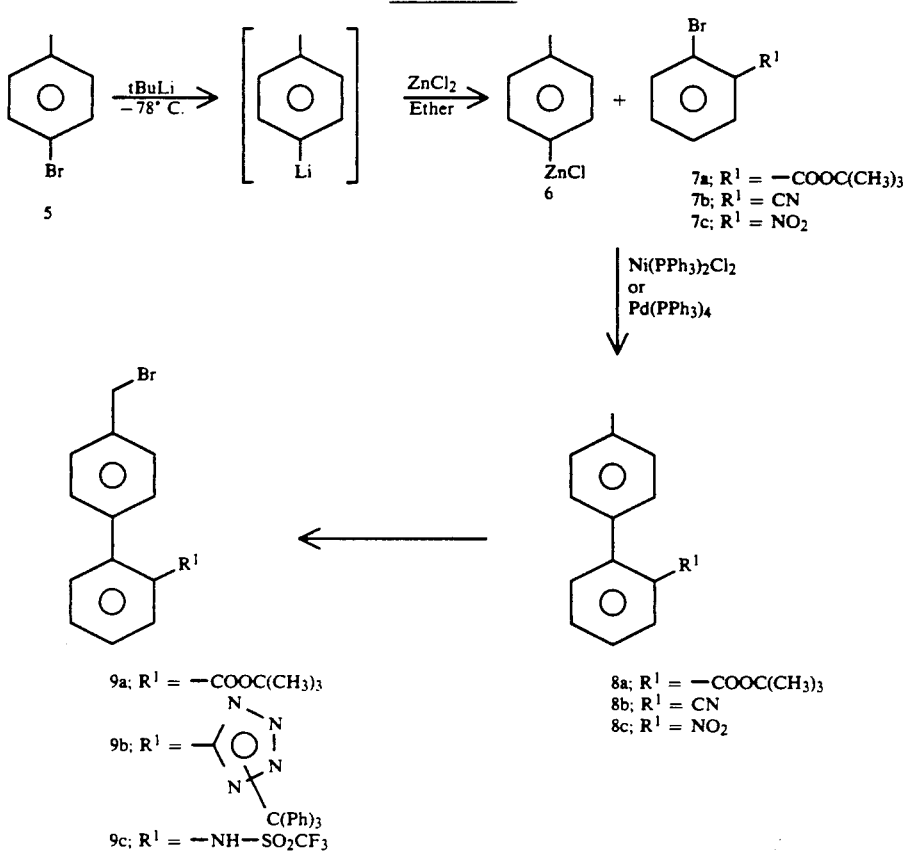

When there is additional substitution on the second phenyl ring ($R^{2a}$, $R^{2b}$=hydrogen) the preferred method to prepare the biphenyl precursors 8d and 8e, using the Pd(O) catalyzed cross-coupling reaction [J. K. Stille, *Angrew, Chem. Int. Ed. Engl.*, 25, 508 (1986)], is outlined in reaction Scheme 2a. As shown in reaction Scheme 2a, p-tolyltrimethyltin (6a) is coupled with 7d or 7e in refluxing toluene in the presence of 5 mole % of Pd(PPh$_3$)$_4$ to produce the desired biphenyl compounds 8d and 8e. Table I illustrates the synthetic utility of this protocol. Compounds 8d ($R^2$=NO$_2$) and 8e ($R^2$=NO$_2$) could be converted to their respective chlorides by catalytic hydrogenation, diazotization and treatment with copper (I) chloride. The biphenyl fluorides which could not be obtained by direct coupling to a fluoro arylbromide were prepared from 8d ($R^2$=NO$_2$) and 8e ($R^2$=NO$_2$) via reduction, formation of the diazonium tetrafluoroborate salt and thermal decomposition. These precursors 8d ($R^2$=NO$_2$ or F or Cl) and 8e ($R^2$=NO$_2$ or F or Cl) are then transformed into the halomethyl biphenyl derivatives 9d and 9e, respectively according to the procedures described in European Patent Applications 253,310 and 292,969.

SCHEME 2a

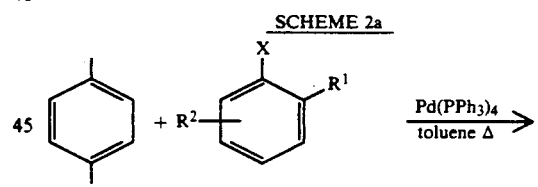

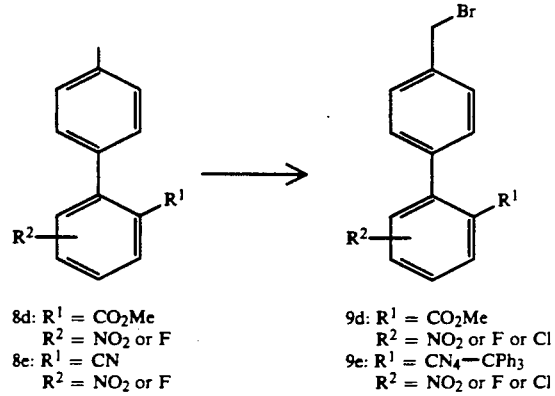

TABLE I
Biphenyl Synthesis

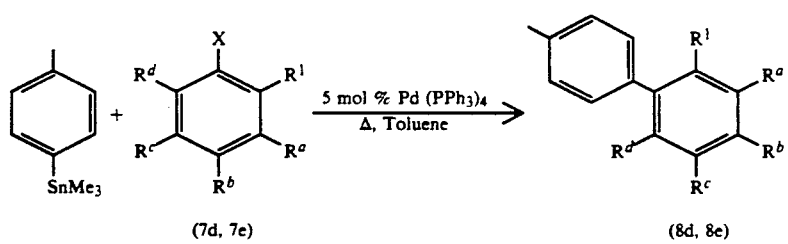

| X | $R^1$ | $R^a$ | $R^b$ | $R^c$ | $R^d$ | Product ($R^a$) | Rf (solvent) | Yield |
|---|---|---|---|---|---|---|---|---|
| Br | CO$_2$Me | NO$_2$ | H | H | H | 8d (3'-nitro) | 0.35 (15:1 Hex/EtOAc) | 71% |
| Br | CN | H | NO$_2$ | H | H | 8e (4'-nitro) | 0.62 (2 × 6:1 Hex/EtOAc) | 74% |
| Br | CO$_2$Me | H | F | H | H | 8d (4'-fluoro) | 0.43 (15:1 Hex/EtOAc) | 83% |
| Cl | CO$_2$Me | H | H | NO$_2$ | H | 8d (5'-nitro) | 0.22 (15:1 Hex/EtOAc) | 70% |
| Br | CO$_2$Me | H | H | H | NO$_2$ | 8d (6'-nitro) | 0.24 (15:1 Hex/EtOAc) | 79% |
| Br | CN | H | F | H | H | 8e (4'-fluoro) | 0.44 (15:1 Hex/EtOAc) | 64% |
| Cl | CN | H | H | F | H | 8e (5'-fluoro) | 0.40 (15:1 Hex/EtOAc) | 62% |

Scheme 3 provides the method by which the isomeric (wherein K is —C(O)—) 2,3,5, and 6-substituted pyrimidinones may be synthesized. A β-carbonyl ester is converted into its corresponding β-aminocrotonate with ammonia.[3] This is then acylated with an $R^6$-containing acyl chloride ($R^6$COCl) and cyclized to a 3,1-oxazin-4-one 10. When the 3,1-oxazin-4-one is reacted with the biphenyl amine 11 the desired fully substituted pyrimidinone 12 results.[4]

SCHEME 3

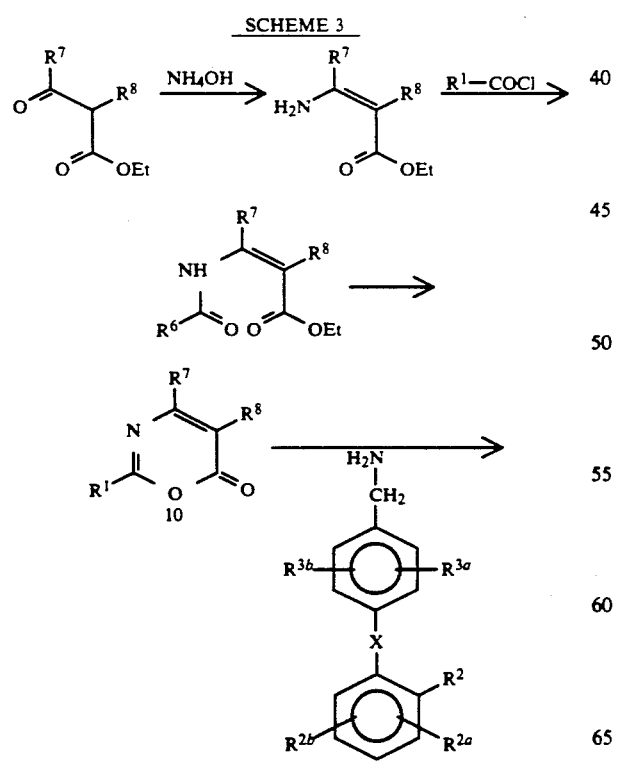

-continued
SCHEME 3

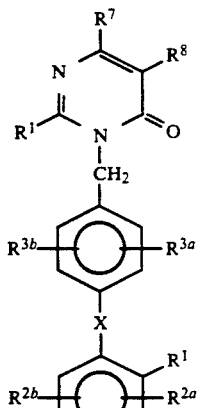

Alternatively, Scheme 4 shows how an $R^6$ imidate 13 may be converted to an amidine 14 with the biphenylamine 11 followed by treatment with an appropriately substituted β-carbonyl ester to give the desired pyrimidinone 12.[5]

SCHEME 4

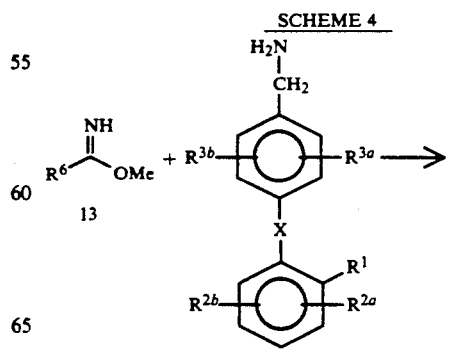

-continued
SCHEME 4

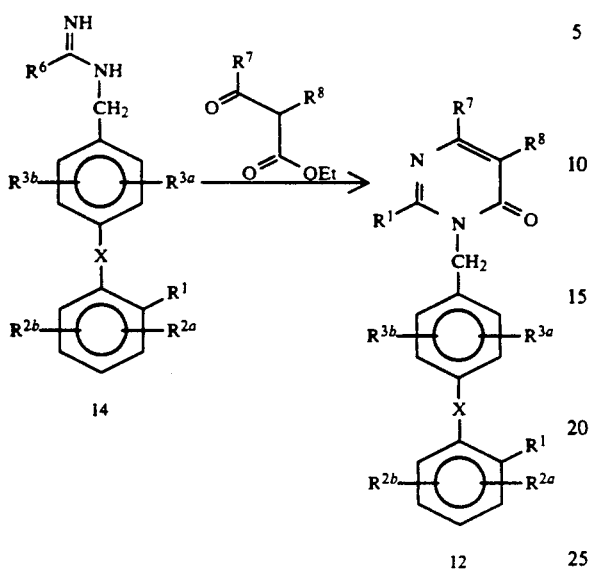

A third alternative is illustrated in Scheme 5. A simple $R^6$ amidine 15 can be reacted with an appropriately substituted β-carbonyl ester to give the 3-unsubstituted 1,4-dihydro-4-oxopyrimidine 16. This can then be alkylated at the 3-position with the appropriately substituted alkyl halide 3 in the presence of KOH in methanol (or with NaH in DMF) to give 12.

SCHEME 5

-continued
SCHEME 5

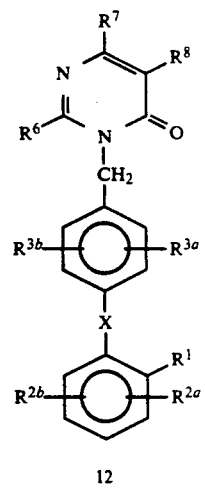

Scheme 6 illustrates the general synthesis of pyrimidinones where E=S. Thiourea when condensed with a β-carbonyl ester gives the 2-thiouracil 17. This can be bis-trimethylsilylated using hexamethyldisilazane and then alkylated sequentially on the 1-nitrogen and then on the sulfur using chemistry developed by H. Vorbruggen and P. Strehlke.[6] By this method, one can obtain compounds 20 wherein J is —C(O)— and E is S.

SCHEME 6

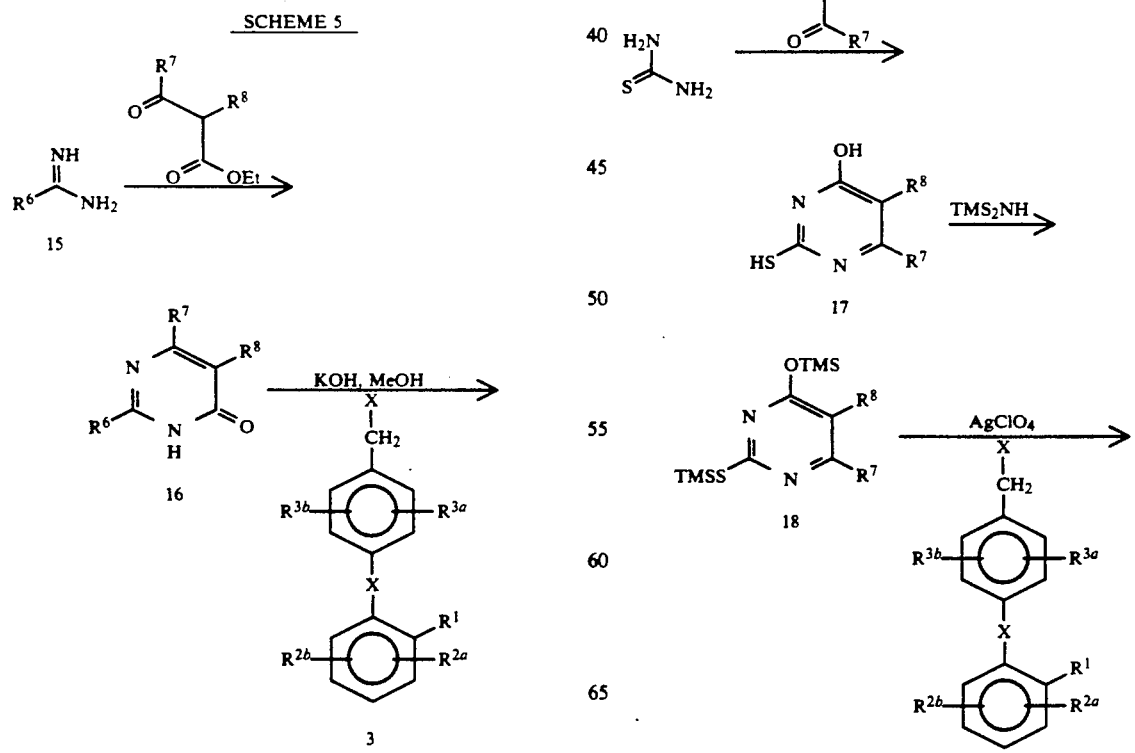

-continued
SCHEME 6

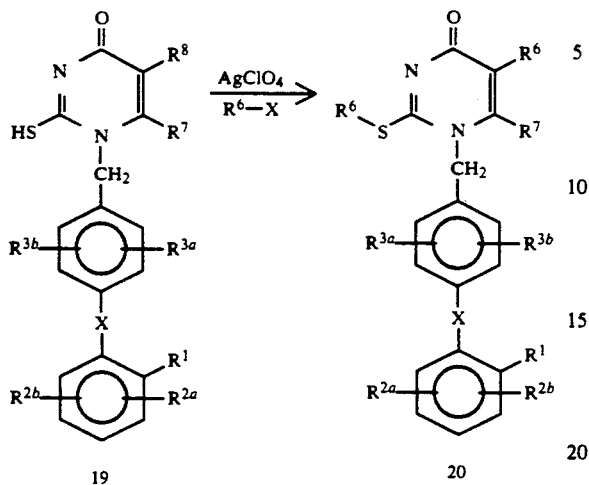

The isomeric 2,3-dialkylated thiouracils may be synthesized as shown in Scheme 7. Thiourea can be condensed with an appropriately substituted β-carbonyl ester to give the 5,6-disubstituted-2-thiouracil 21.[7] This may then be alkylated sequentially on the sulfur with an R[6] halide then on the nitrogen with an appropriately substituted alkyl halide 3 to give the desired tetrasubstituted pyrimidinone 23.

-continued
SCHEME 7

Alternatively, as illustrated in Scheme 8, an isothiocyanate 24 can be made into a thiourea 25 by the addition of ammonia.[8] This can then be condensed with the appropriately substituted β-carbonyl ester to give the 3,5,6-trisubstituted-2-thiouracil 26.[9] Alkylation of the sulfur atom then with base and an R[6] halide gives the desired pyrimidinone 23.

SCHEME 7

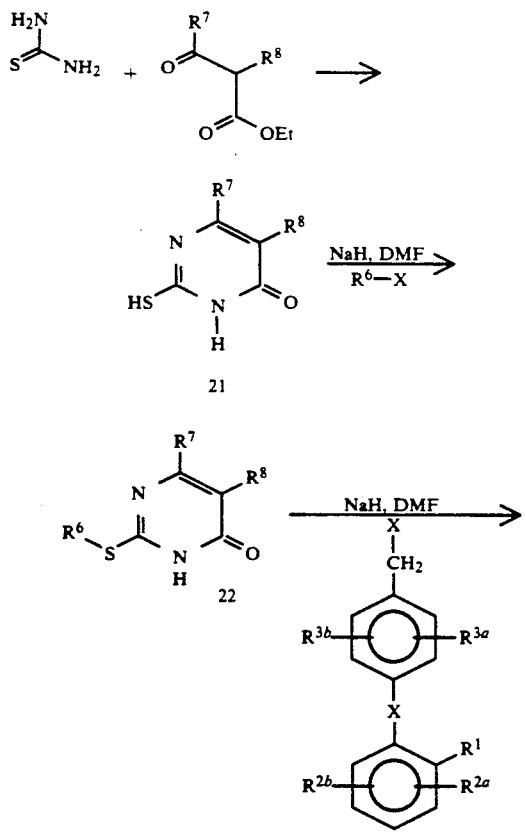

SCHEME 8

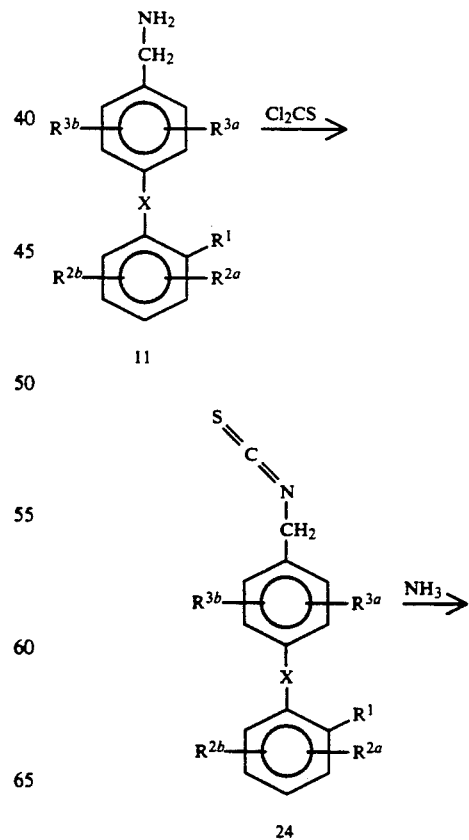

-continued
SCHEME 8

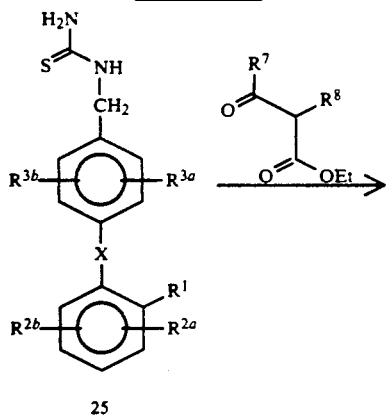

25

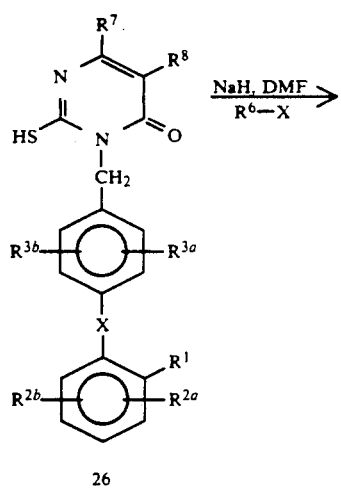

26

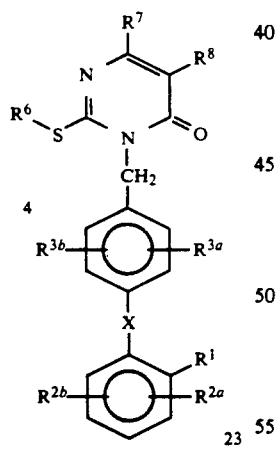

23

SCHEME 9

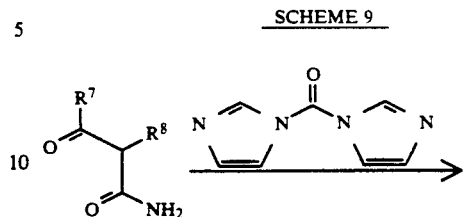

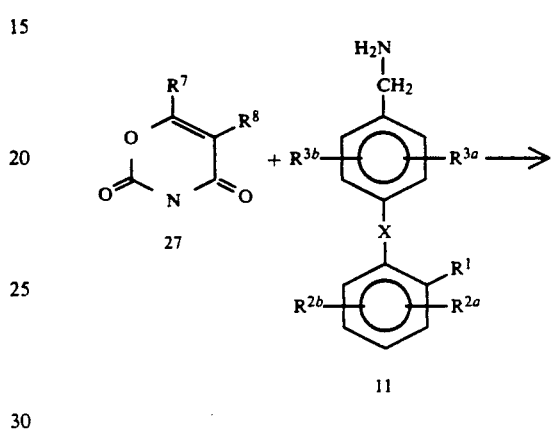

11

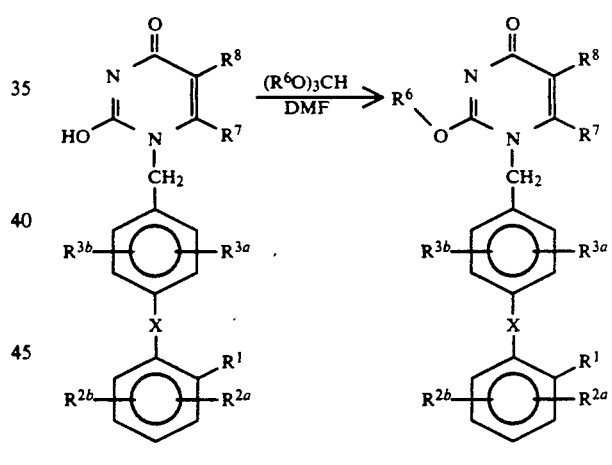

28                29

SCHEME 10

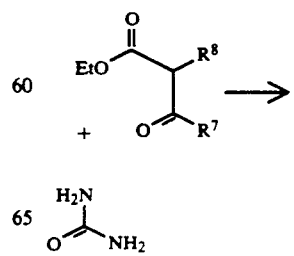

Scheme 9 provides a method by which the 2-alkoxy-1-alkylpyrimidinones 29 may be synthesized. An appropriately substituted β-keto amide[10] is cyclized with carbonyl diimidazole[11] and the product 23 is converted to the corresponding uracil 28 upon treatment with the appropriately substituted primary amine 3.[12] The uracil can then be converted to the 2-alkoxy-1-alkylpyrimidinone 29 with an $R^6$ orthoester.[13] Alternatively, Scheme 10 shows how the methods of Wittenburg[14] might be employed to accomplish the same transformation.

SCHEME 10 -continued

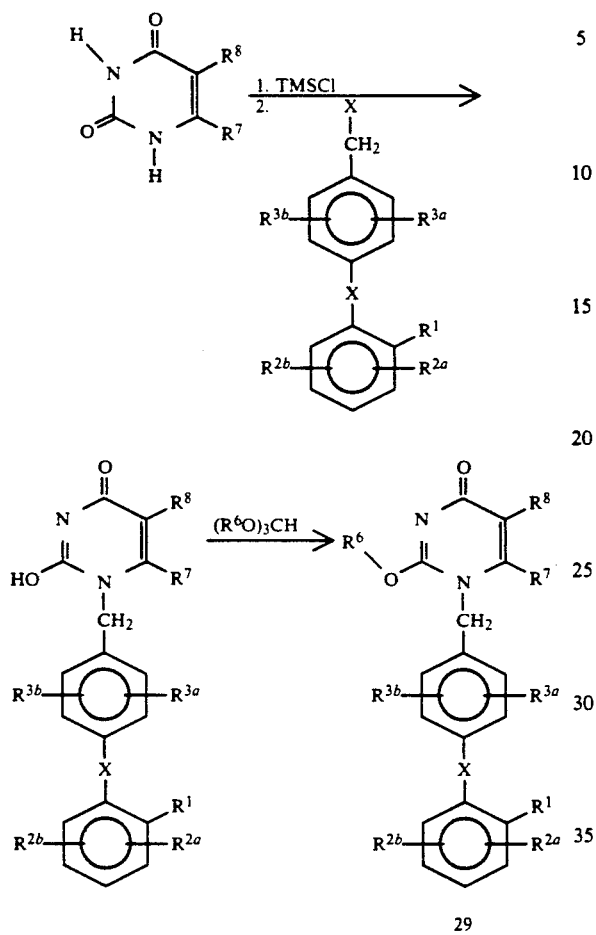

SCHEME 11

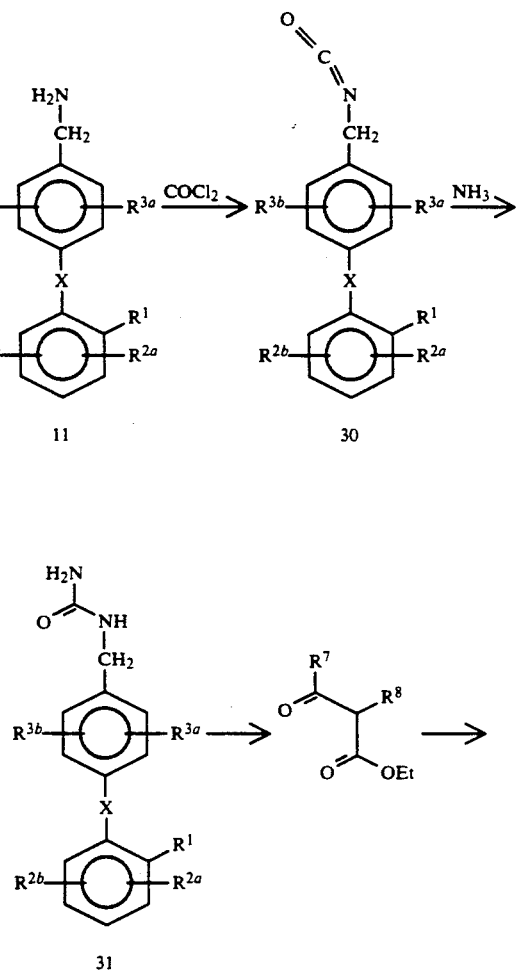

Scheme 11 shows how the isomeric 2-alkoxy-3-alkyl-pyrimidinones 33 can be prepared. The primary amine 11 can be made into its isocyanate 30[15], then transformed into the corresponding urea 31 with ammonia. Reaction of the urea with an appropriately substituted β-keto ester gives the 3-substituted uracil 32.[16] Conversion of the uracil to the corresponding 2-alkoxy pyrimidinone 33 is achieved using an $R^6$ orthoester.[17] Alternatively, a β-aminocrotonate 34 can be reacted with the isocyanate, as shown in Scheme 12[18] and then alkoxylated with an $R^6$ orthoester.

The β-keto esters used in the preceding schemes can be synthesized readily from ethyl hydrogen malonate and an $R^7$ acid chloride as shown in Scheme 13.[19] $R^7$ may be alkyl or aryl. Alkylation of this material with an $R^8$ alkyl halide is achieved using sodium hydride in DMSO or by other classical methods. $R^8$ may be alkyl or arylalkyl suitably protected, if necessary, so as not to react with NaH. Scheme 14 illustrates the preparation of the 5-alkoxycarbonyl derivative 35 and the corresponding 5-amino derivatives 36.

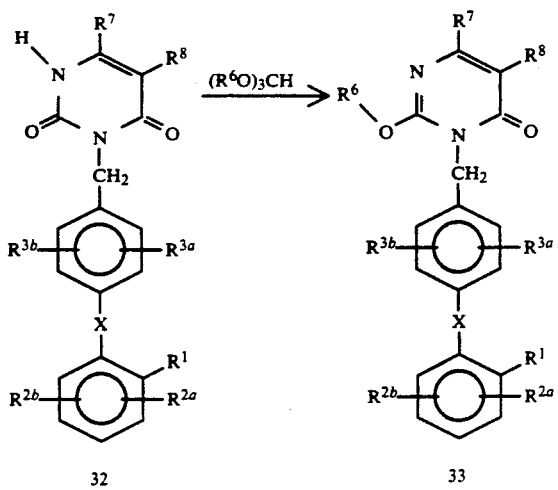

SCHEME 12

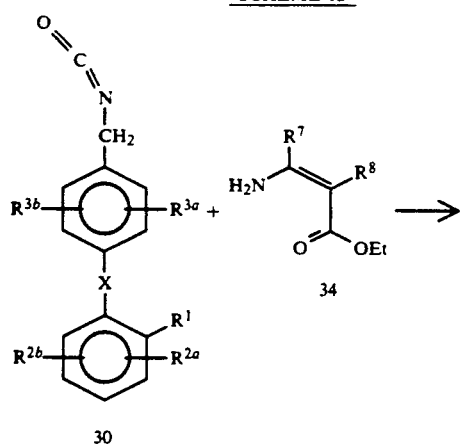

SCHEME 13

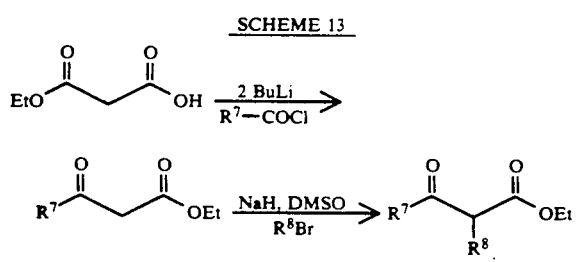

SCHEME 14

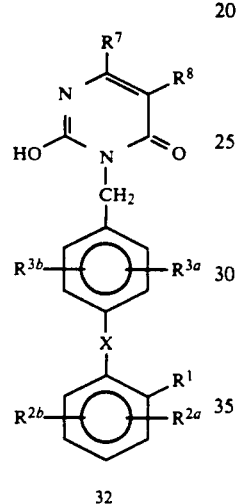

-continued
SCHEME 14

Hofmann, Curtius, or Schmidt Rearrangements

Compounds of formula I where $R^1$ is —CONHSO$_2$R$^{21}$ (where $R^{21}$=alkyl, aryl or heteroaryl) may be prepared from the corresponding carboxylic acid derivatives 37 as outlined in Scheme 15. The carboxylic acid 37 prepared using the methods described in Schemes 1–14, can be converted into the corresponding acid chloride by treatment with refluxing thionyl chloride or preferably with oxalylchloride and a catalytic amount of dimethylformamide at low temperature [A. W. Burgstahler, L. O. Weigel, and C. G. Shaefer—*Synthesis*, 767, (1976)]. The acid chloride then can be treated with the alkali metal salt of $R^{21}SO_2NH_2$ to form the desired acylsulfonamide 38. Alternatively, these acylsulfonamides may be also prepared from the carboxylic acids using N,N-diphenylcarbamoyl anhydride intermediates [F. J. Brown et al—European Patent Application, EP 199543; K. L. Shepard and W. Halczenko—*J. Het. Chem.*, 16, 321 (1979)]. Preferably the carboxylic acids can be converted into acyl-imidazole intermediates, which then can be treated with an appropriate aryl or alkylsulfonamide and diazabicycloundecane (DBU) to give the desired acylsulfonamide 38. [J. T. Drummond and G. Johnson—*Tetra. Lett.*—29, 1653 (1988)].

SCHEME 15
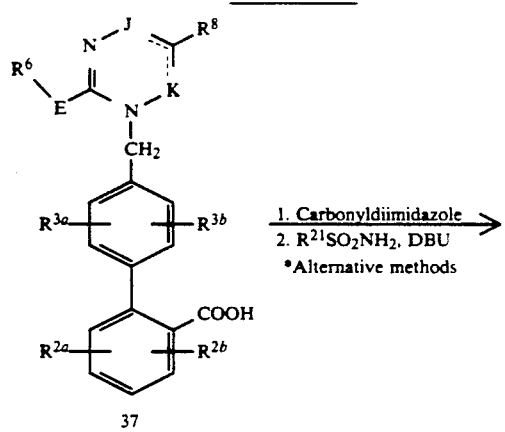
37
1. Carbonyldiimidazole
2. $R^{21}SO_2NH_2$, DBU
*Alternative methods
-continued
SCHEME 15
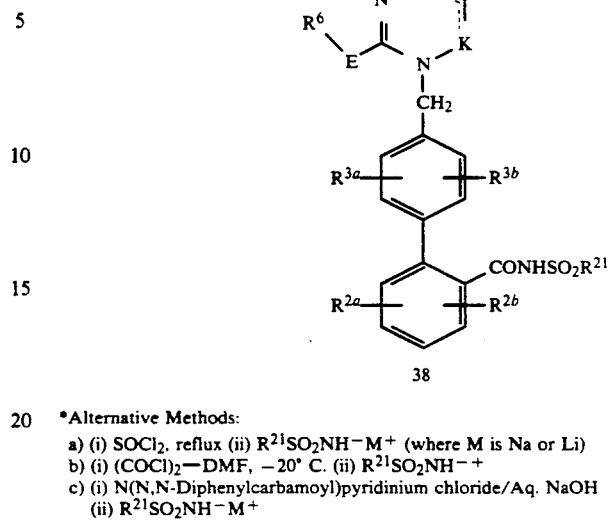
38
*Alternative Methods:
a) (i) $SOCl_2$, reflux (ii) $R^{21}SO_2NH^-M^+$ (where M is Na or Li)
b) (i) $(COCl)_2$—DMF, −20° C. (ii) $R^{21}SO_2NH^-$
c) (i) N(N,N-Diphenylcarbamoyl)pyridinium chloride/Aq. NaOH
   (ii) $R^{21}SO_2NH^-M^+$
SCHEME 16
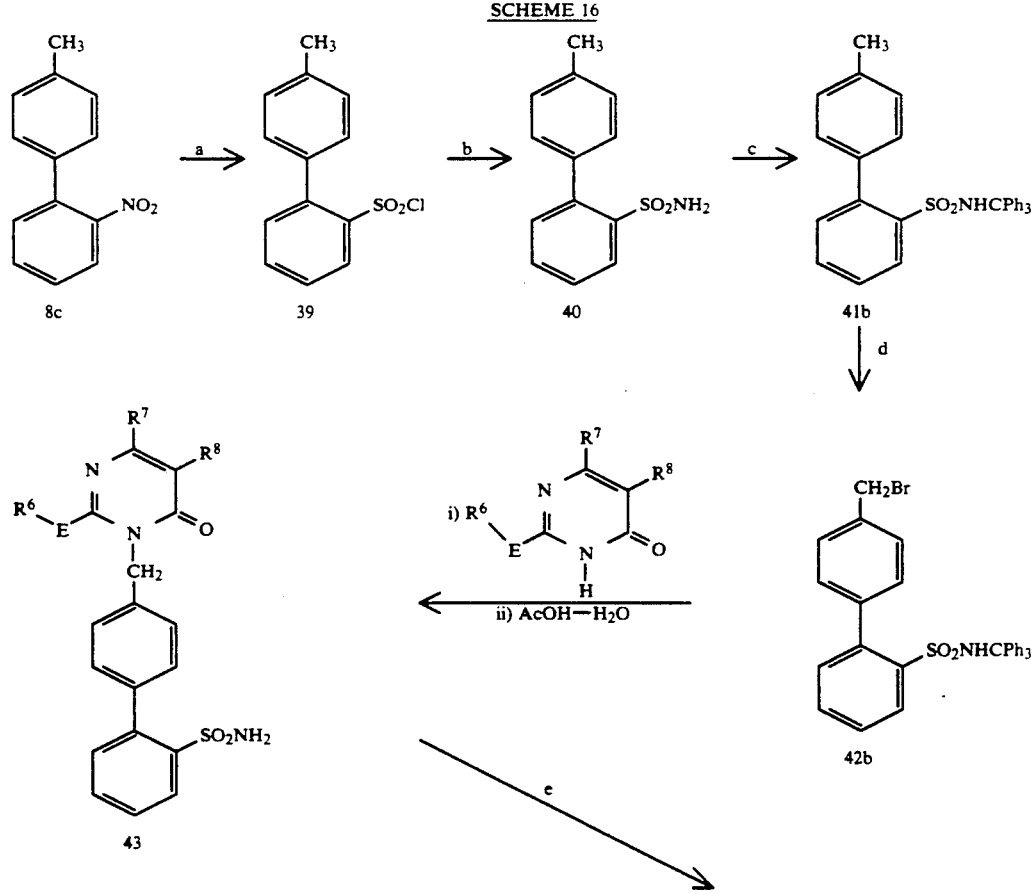

SCHEME 16 -continued

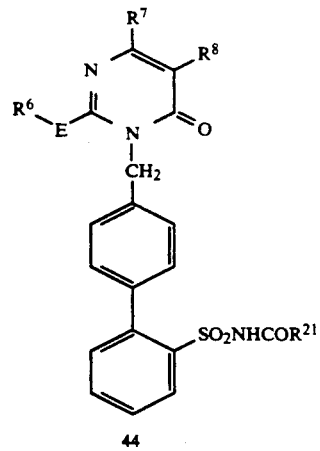

a. i) $H_2$/Pd—C, ii) $NaNO_2$—HCl, iii) $SO_2$, AcOH, $CuCl_2$
b. $NH_3$ or $(NH_4)_2CO_3$
c. $Ph_3CCl$, $Et_3N$, $CH_2Cl_2$, 25° C.
d. N-Bromosuccinimide
e. $R^{21}COCl$ or $R^{21}CO$—Im or other acylating agents Compounds of formula I where $R^1$ is —$SO_2$NHCOR$^{21}$ may be prepared as outlined in Scheme 16. The nitro compound 8c (prepared as described in Scheme 2) can be reduced to the corresponding amino compound and converted into aromatic diazonium chloride salt, which then can be reacted with sulfur-dioxide in the presence of a copper(II) salt to form the corresponding arylsulfonylchloride 39 [H. Meerwein, G. Dittmar, R. Gollner, K. Hafner, F. Mensch and O. Steifort—Chem. Ber., 90, 841 (1957); A. J. Prinsen and H. Cerfontain, Recueil, 84, 24 (1965); E. E. Gilbert, Synthesis, 3 (1969) and references cited therein]. The sulfonyl chloride can be reacted with ammonia in aqueous solution or in an inert organic solvent [F. H. Bergheim and W. Baker, J. Amer. Chem. Soc., 66, (1944), 1459], or with dry powdered ammonium carbonate, [E. H. Huntress and J. S. Autenrieth, J. Amer. Chem. Soc.., 63, (1941), 3446; E. H. Huntress and F. H. Carten, J. Amer. Chem. Soc., 62, (1940), 511] to form the sulfonamide 40. The benzylbromide 42b may be prepared from the sulfonamide 40 as outlined in Scheme 16, and then can be reacted with an alkali metal salt of an appropriate heterocyclic compound to form the key sulfonamide 43. The sulfonamide 43 may be also prepared from the aromatic sulfonyl chloride 48, which may be prepared from the aryl amine 47 as outlined in Scheme 17. The acylation of 43 with appropriate acyl chlorides (or acyl-imidazoles or other acylating agents) may produce the desired acyl-sulfonamides 44.

The compounds (49) bearing $R^1$ as —$SO_2$NHR$^{21}$ (where $R^{21}$ is heteroaryl) may be prepared by reacting the aromatic sulfonyl chloride 48 with appropriate heteroaryl amines as outlined in Scheme 17.

SCHEME 17

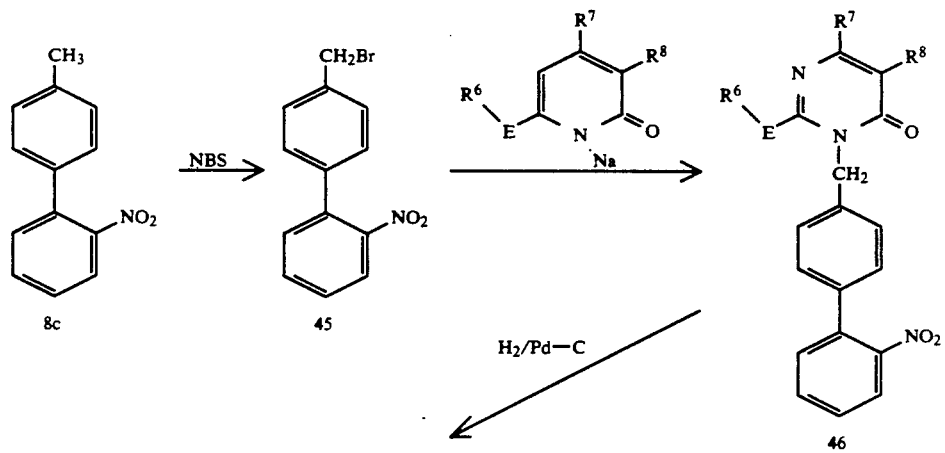

-continued
SCHEME 17

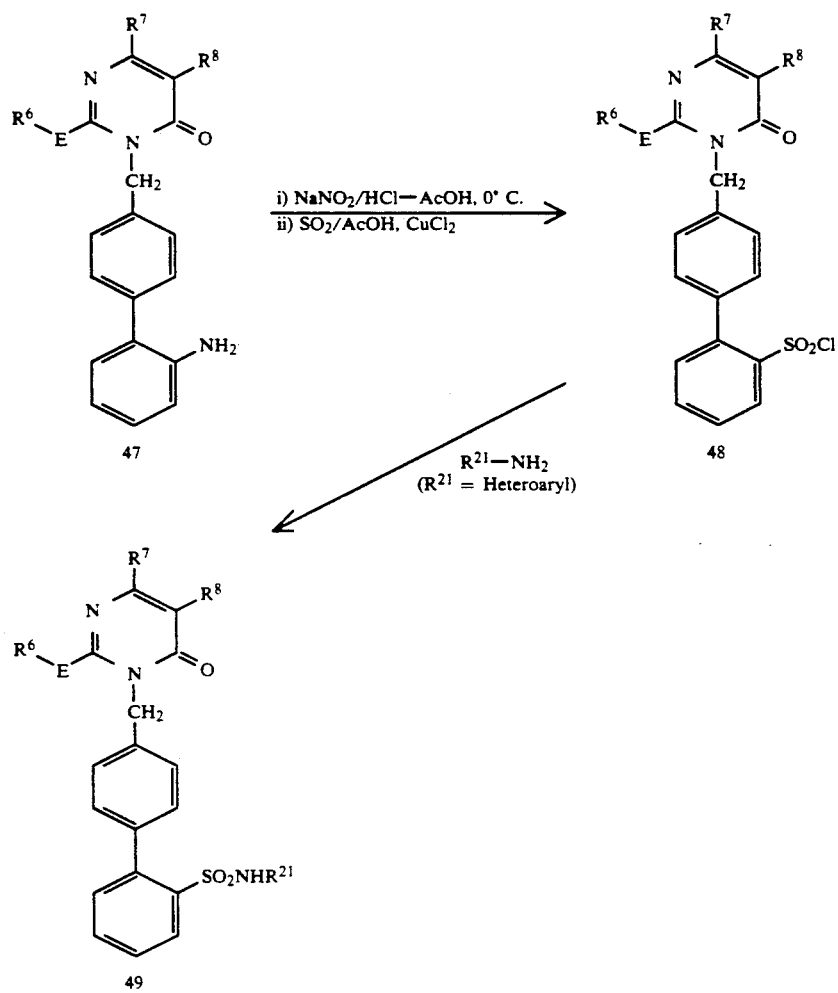

The sulphenyl chloride 48 may be the preferred intermediate for the synthesis of this class of compounds. The aromatic sulfonyl chlorides may also be prepared by reacting the sodium salt of aromatic sulfonic acids with $PCl_5$ or $POCl_3$ [C. M. Suter, *The Organic Chemistry of Sulfur*, John Wiley & sons, 459, (1944)]. The aromatic sulfonic acid precursors may be prepared by chlorosulfonation of the aromatic ring with chlorosulfonic acid [E. H. Huntress and F. H. Carten, *J. Amer. Chem. Soc.*, 62, 511 (1940)].

The biaryl sulfonamides 41a and 41b (described in Scheme 16) can be prepared alternatively using palladium (0) catalyzed cross-coupling reactions of appropriate aryl-organotin precursors [J. K. Stille, *Pure Appl. Chem.*, 57, 1771 (1985); T. R. Baiely, *Tetra Lett.*, 27, 4407 (1986); D. A. Widdowson and Y. Z. Zhang, *Tetrahedron*, 42, 2111 (1986)], as outlined in Scheme 18. The organotin compound 51 [S. M. Moerlein, J. Organometallic Chem., 319, 29 (1987)], obtained from the aromatic precursor 50, may be coupled with aryl sulfonamides 53 and 54 using $Pd(PPh_3)_4$ or $(PPh_3)_2PdCl_2$ as catalysts to give biaryl sulfonamides 41a and 41b alternatively prepared from the appropriate organotin precursor 57 using the Pd(0) catalyzed cross-coupling reaction as outlined in Scheme 19.

SCHEME 18

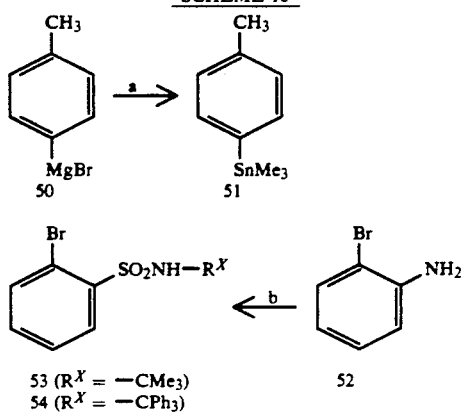

SCHEME 18

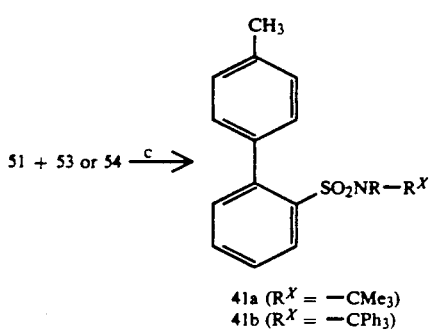

51 + 53 or 54 —c→

41a ($R^X$ = —CMe$_3$)
41b ($R^X$ = —CPh$_3$)

a. Me$_3$SnCl b. (i) NaNO$_2$/HCl (ii) SO$_2$, CuCl$_2$ c. Pd(PPh$_3$)$_4$, Toluene or (PPh$_3$)$_2$PdCl$_2$, DMF, 90° C.

SCHEME 19

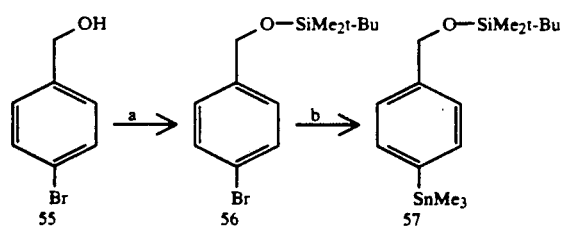

55 → 56 → 57

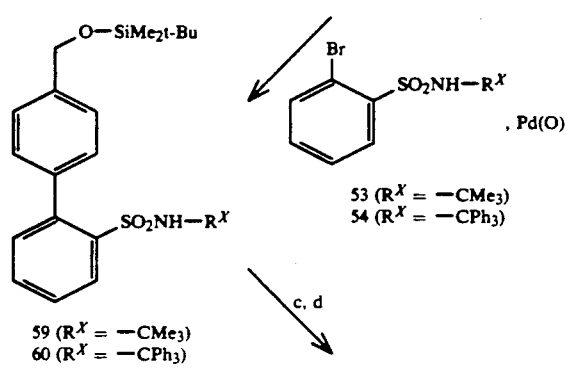

59 ($R^X$ = —CMe$_3$)
60 ($R^X$ = —CPh$_3$)

53 ($R^X$ = —CMe$_3$)
54 ($R^X$ = —CPh$_3$)

-continued
SCHEME 19

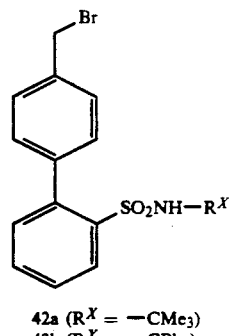

42a ($R^X$ = —CMe$_3$)
42b ($R^X$ = —CPh$_3$)

a. t-Bu Me$_2$SiCl/Imidazole, DMF
b. t-BuLi, −78° C., Me$_3$SnCl
c. Tetrabutylammonium fluoride
d. CBr$_4$/Ph$_3$P The compounds bearing $R^1$=—CH$_2$CO$_2$NHCOR$^{21}$ and —CH$_2$SO$_2$NHR$^{21}$ may be prepared as outlined in Scheme 20. The key precursor aryl-methanesulfonyl chloride 67 may be prepared either from the reaction of aryl-methylmagnesium chloride 66 (obtained from the corresponding benzyl chloride 63) with sulfurylchloride [S. N. Bhattacharya, C. Eaborn and D. P. M. Walton, J. Chem. Soc. C, 1265 (1968)], or by oxidation of the aryl-methylthioacetate 65 (prepared from the benzyl bromide 64) with chlorine in presence of trace amount of water [Bagnay and Dransch, Chem. Ber., 93, 784 (1960)]. Alternatively, the aryl-methylthioacetate 65 can be oxidized with sulfuryl chloride in presence of acetic anhydride to form aryl-methylsulfinyl chloride [S. Thea and G. Cevasco, Tetra. Lett., 28, 5193 (1987)], which can be further oxidized with appropriate oxidizing agents to give the sulfonyl chloride 67. The compound 69 can be obtained by reacting the sulfonyl chloride 67 with appropriate amines. The compound 68 may be prepared by the acylation of the primary sulfonamide (compound 68a, where $R^Y$=H).

Compounds where $R^1$=—NHSO$_2$NHR$^{21}$ may be prepared by the reaction of appropriate primary amines with the sulfamide 71 [S. D. McDermott and W. J. Spillane, Synthesis, 192 (1983)], as described in Scheme 21. The compound 71 may be obtained from the corresponding N-t-butylsulfamide 70 after treatment with anhydrous trifluoroacetic acid [J. D. Catt and W. L. Matier, J. Org. Chem., 39, 566 (1974)], which may be prepared by the reaction of the aromatic amine 47 with t-butylsulfamoyl chloride [W. L. Matier, W. T. Comer and D. Deitchman, J. Med. Chem., 15, 538 (1972)].

SCHEME 20
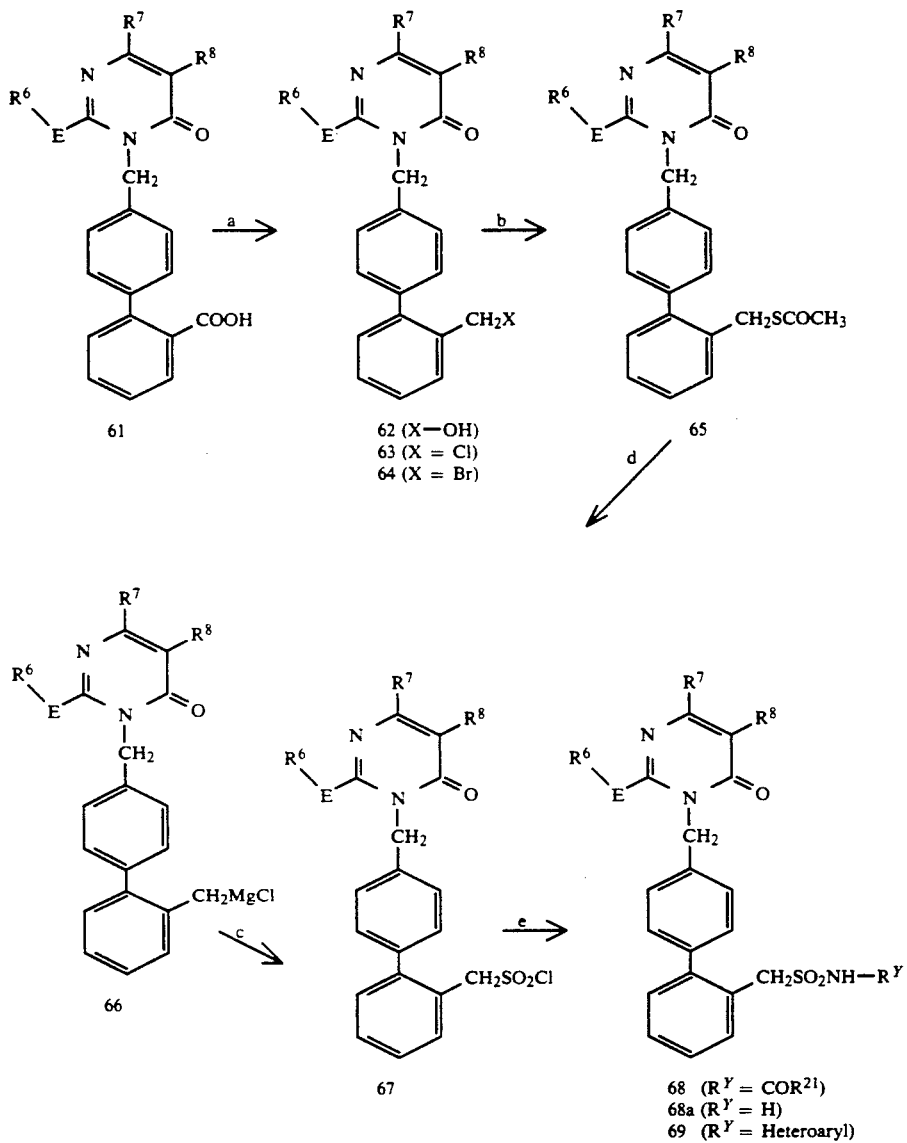
a. i) EtOCOCl/Et₃N, THF, 0° C. ii) NaBH₄
iii) CCl₄ or CBr₄/PPH₃
b. AcSK
c. SO₂Cl₂
d. Cl₂, AcOH, H₂O or, i) SO₂Cl₂ ii) oxidation
e. R^Y NH₂ or, i) NH₃ ii) Acylation SCHEME 21
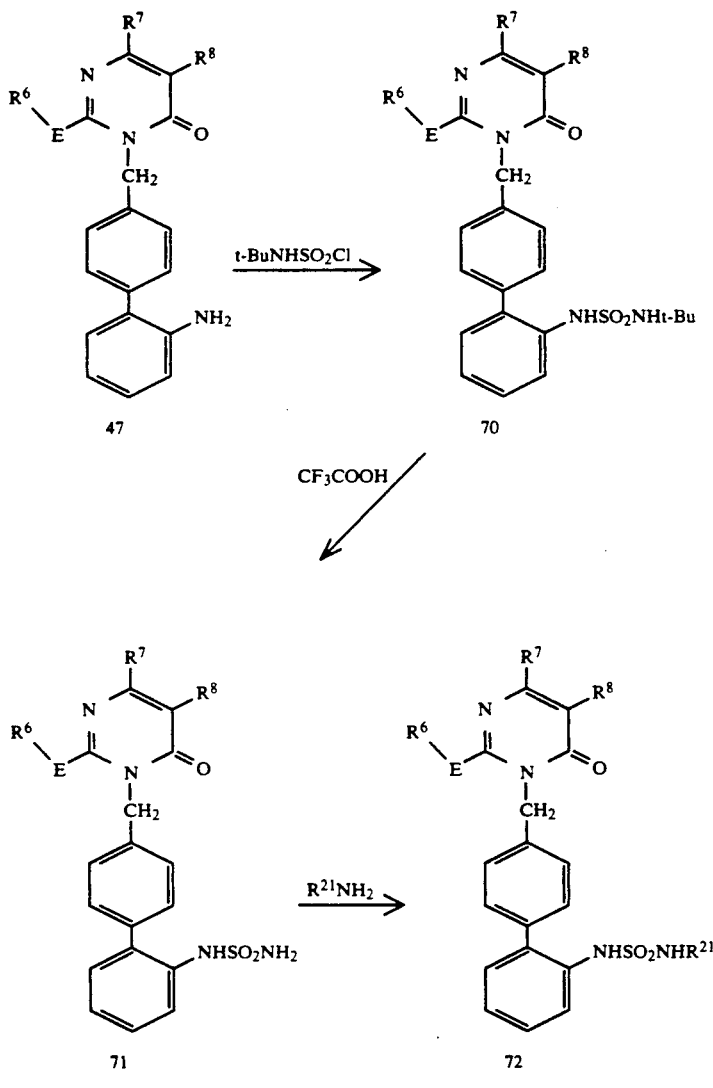
Scheme 22 illustrates how 5-methylenecarbamoyl-pyrimidinones 75 and 76 could be prepared from the corresponding 5-carboalkoxy derivative 73 using common derivatization methods.

SCHEME 22

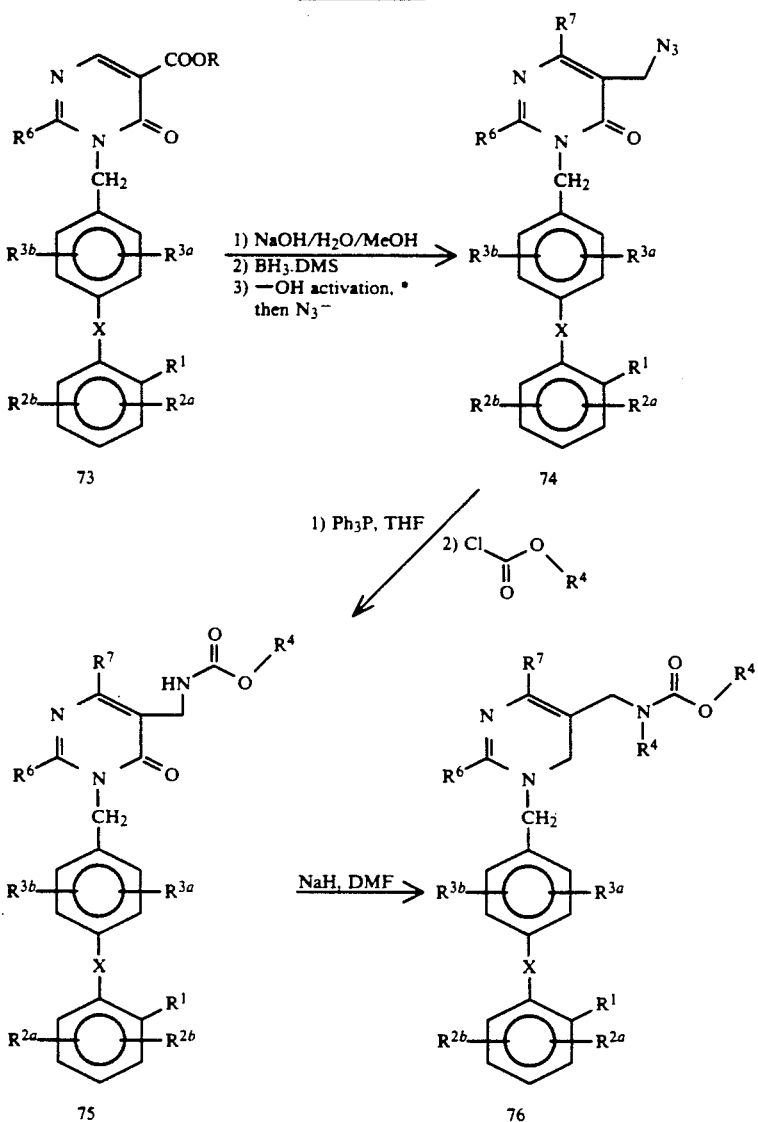

* Y. Tanigawa, et al. Tet. Lett., 471 (1975)
S. Pilard, et al, Tet. Lett., 25, 1555 (1984)
G. W. J. Fleet, et al. Tet. Lett., 27, 3057 (1986)

1. K. Wunsch, A. J. Boulton, *Adv. Het. Chem.* (1967), 8, 326-9 and references therein.
2. D. J. Brown, E. Hoerger, S. F. Mason, *J. Chem. Soc.* (1955), 4035.
3. V. Prelog, et al, Ber. (1945), 28, 1684.
4. H. B. Kagan, M. Y. H. Suen, *Bull. Soc. Chim. Fr.* (1966), 1819. W. Steglich, E. Buschmann, O. Hollitzer, *Angew. Chem. Int. Ed. Engl.* (1974), 13, 533. F. Eiden, B. S. Nagar, *Naturwissenschaften* (1963), 50, 43. A. Krantz, B. Hoppe, *J. Am. Chem. Soc.* (1975), 97, 6590.
5. A. Sitte, H. Paul, *Chem. Ber.* (1969), 102, 615.
6. H. Vorbruggen, P. Strehlke, *Chem. Ber.* (1973), 106, 3039.
7. D. J. Brown, The Pyrimidines, (1962), J. Wiley & Sons, p. 300.
8. D. J. Brown, The Pyrimidines, (1962), J. Wiley & Sons, p. 437.
9. R. G. Dave, G. S. Mewada, G. C. Amin, *J. Ind. Chem. Soc.* (1960), 37, 595. M. Sano, *Chem. Pharm. Bull.* (1962), 10, 313. C. Piantadosi, V. G. Skulason, J. L. Irvin, J. M. Powell, L. Hall, *J. Med. Chem.* (1964), 7, 337.
10. M. K. Jain, *Ind. J. Chem.* (1963), 1, 274. P. C. Kuzma, L. E. Brown, T. M. Harris, *J. Org. Chem.* (1984), 49, 2015.
11. S. De Bernardo, M. Weigele, *J. Org. Chem.* (1977), 42, 109.
12. T. Kinoshita, H. Tanaka, S. Furukawa, *Chem. Pharm. Bull.* (1986), 34, 1809.
13. F. Yoneda, T. Nagamatsu, M. Takamoto, *Chem. Pharm. Bull.* (1983), 31, 344.
14. Wittenburg, *Angew. Chem.* (1965), 77, 1043.
15. S. Ozaki, *Chem. Rev.* (1972), 72, 457.
16. Gabriel, Colman, Ber. (1904), 37, 3657.
17. F. Yoneda, T. Nagamatsu, M. Takamoto, *Chem. Pharm. Bull.* (1983), 31, 344.
18. R. Behrend, F. C. Meyer, Y. Buckholz, *Liebigs Ann. Chem.* (1901), 314, 200.
19. W. Wierenga, H. I. Skulnick, *Org. Syn.* (1983) 615.

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which, in the last step, is removed by treatment with trifluoroacetic acid. Aqueous acetic acid employed overnight is a preferred method to remove a trityl protecting group to liberate an $R^1$ tetrazole group.

The compounds of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluensulfonic, maleic, fumaric, camphorsulfonic. The non-toxic, physiologically acceptable salts are preferred, although other salts are also useful, e.g., in isolating or purifying the product.

The salts can be formed by conventional means such as by reacing the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

RECEPTOR BINDING ASSAY USING RABBIT AORTAE MEMBRANE PREPARATION

Three frozen rabbit aortae (obtained from Pel-Freeze Biologicals) were suspended in 5 mM Tris-0.25M Sucrose, pH 7.4 buffer (50 ml), homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin, and the suspension was used for 100 assay tubes. Samples tested for screening were done in duplicate. To the membrane preparation (0.25 ml) there was added $^{125}I$-Sar$^1$Ile$^8$-angiotensin II [obtained from New England Nuclear] (10 μl; 20,000 cpm) with or without the test sample, and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist, which gives 50% displacement of the total specifically bound $^{125}I$-Sar$^1$Ile$^8$-angiotensin II, was presented as a measure of the efficacy of such compounds as AII antagonists.

RECEPTOR ASSAY USING BOVINE ADRENAL CORTEX PREPARATION

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds generally duplicates of tubes are used). To the membrane preparation (0.5 ml) there was added 3H-angiotensin II (50 mM) (10 μl), with or without the test sample, and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist, which gives 50% displacement of the total specifically bound $^3H$-angiotensin II, was presented as a measure of the efficacy of such compounds as AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propanolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention were evaluated and were found to exhibit an activity of at least $IC_{50} < 50$ μM, thereby demonstrating and confirming the utility of the compounds of the invention as effective AII antagonists.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, and in the management of vascular disorders such as migraine, Raynaud's disease, luminal hyperclasia and to minimize the atherosclerotic process.

The application of the compounds of this invention for these and similar disorders will be apparent to those skilled in the art.

The compounds of this invention are, also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient, depending upon the nature and severity of disease, the patient's weight, special diets then being followed by a patient, concurrent medication and other factors, which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, Rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-300 Fourier transform spectrometer or on a Bruker 250 MHz spectrometer. Chemical shifts are reported as (parts per million) downfield from tetramethyl silane. Mass spectra were obtained from the Merck and Co. mass spectral facility in Rahway N.J. Analytical TLC was conducted on E. M.

Merck precoated silica plates (0.25 mm in glass, Kieselgel 60 F254) with UV visualization. All chromatography was conducted on E. M. Merck silica gel. All reactions were carried out under an atmosphere of dry nitrogen under standard conditions for those skilled in the art.

PREPARATION OF INTERMEDIATES

Methyl Valerimidate Hydrochloride

Into a solution of 100 g valeronitrile in 1 L anhydrous methanol was bubbled anhydrous HCl for 105 minutes at 0° C. The mixture was allowed to warm to room temperature and stir overnight. The excess HCl and methanol were removed in vacuo. The white solid was suspended in 1500 mL ether and then suction filtered. The solid was washed with an additional 400 mL ether. The solid product was then placed in a vacuum desiccator overnight at 5 Torr to give 128.5 g of a flocculent, white, deliquescent solid, 70% yield.

Valeramidine Hydrochloride

Into a solution of 40 g methyl valerimidate hydrochloride in 500 mL methanol was bubbled anhydrous ammonia for 1 hour with ice water cooling. The excess ammonia and methanol were removed in vacuo and the product was placed in a vacuum desiccator overnight at 5 Torr to give the amidine salt as a mixture of ~⅔ clear viscous oil and ⅓ crystalline solid. $^1$H NMR (300 MHz, CD$_3$OD) δ2.45 (3 line m, 2H), 1.68 (m, 2H), 1.43 (m, 2H), 0.98 (t, J=7.3 Hz, 3H).

4-Aminomethyl-2'-cyanobiphenyl

A solution of 4.0 g 4-bromomethyl-2'-cyanobiphenyl and 1.43 g sodium azide in 100 mL DMSO was stirred at room temperature for two hours. The mixture was diluted with brine and extracted three times with ether. The combined organic material was washed with brine, dried over MgSO$_4$, and stripped of solvent in vacuo. The crude material was used without further purification.

The crude azide was dissolved in 100 mL of 5% H$_2$O in THF. To this was added 4.24 g triphenylphosphine. After a 5 minute induction period, nitrogen gas was observed evolving from the reaction mixture. After 6 hours, the solvent was removed in vacuo and the crude material was partitioned between 5% HCl and ether. The organic layer was extracted once with 5% HCl. The combined aqueous layers were washed twice with ether. The aqueous material was then made basic with 50% NaOH and then was extracted three times with ether. The combined organic material was dried over Na$_2$SO$_4$, was stripped of solvent in vacuo, and then was Still flash chromatographed in 1 concentrated NH$_4$OH solution/3 methanol/20 hexane/76 CH$_2$Cl$_2$ to give 2.20 g of the title compound as a light yellow crystalline solid $^1$H NMR (300 MHz, CDCl$_3$) δ7.77 (m, 1H), 7.65 (m, 1H), 7.57-7.40 (m, 6H), 3.95 (s, 2H), 1.49 (s, 2H).

N-(2'-cyanobiphen-4-yl)methylvaleramidine

The title compound is prepared by stirring one equivalent of methyl valerimidate hydrochloride, one equivalent of 4-aminomethyl-2'-cyanobiphenyl, and one equivalent of sodium methoxide in methanol. The reaction mixture may then be stripped of solvent and the amidine and residual sodium chloride is used directly in the next reaction.

4-Aminomethyl-2'-t-butoxycarbonylbiphenyl

The title compound is prepared similarly to 4-aminomethyl-2'-cyanobiphenyl except 4-bromomethyl-2't-butoxycarbonylbiphenyl is used in place of 4-aminomethyl-2'-cyanobiphenyl.

2-t-Butoxycarbonyl-4'-methylbiphenyl

To a solution of p-bromotoluene (30 g) in dry ether (150 ml) at −78° C., a solution of t-BuLi in pentane (1.7M) (210 ml) was added slowly over a period of 1.5 hr using a dropping funnel. The bath was then removed and the mixture was stirred at room temperature for an additional 2 hours. The content of the flask was then added slowly (using a cannula) at room temperature to a premixed solution of ZnCl$_2$ in ether (1M, 180 ml) and dry THF (360 ml). The mixture was stirred for 2 hr at that temperature and then the slurry was added (using a cannula) to a solution of 2-t-butoxycarbonyl iodobenzene (35.6 g) and NiCl$_2$(Ph$_3$P)$_2$ (2.1 g) in dry THF (360 ml). The mixture, after stirring at room temperature overnight (18 hr), was poured slowly under stirring into ice-cold 0.5N HCl (1500 ml). The organic layer was separated, and the aqueous phase was extracted with ether (3×300 ml). The combined organic layer was washed with water, brine and then dried over MgSO$_4$. Removal of the solvent gave the crude product as an oil (32 g). The material was purified on a silica-gel flash column using ethyl acetate-hexane (1:12) to give the titled compound as an oil (24 g, 76%). $^1$H NMR (CDCl$_3$): δ1.24 (s, 9H), 2.42 (s, 3H), 7.2-7.8 (m, 8H); FAB-MS: m/e 269 (M+H).

4-Bromomethyl-2'-t-butoxycarbonylbiphenyl

To a solution of 2-t-butoxycarbonyl-4'-methylbiphenyl (25.3 g, 95 mmol) in CCl$_4$ (200 ml) were added freshly opened N-bromosuccinimide (17.6 g, 0.099 mole) and dibenzoyl peroxide (2.28 g, 0.0094 moles). The mixture was refluxed for 4 hours, cooled to room temperature and filtered. The filtrate was washed with sat. NaHSO$_3$ (1×50 ml), sat. NaHCO$_3$ (1×50 ml), water (1×50 ml), sat. NaCl (1×50 ml) and dried over MgSO$_4$. The solution was filtered and concentrated in vacuo. The residue was dissolved in 100 ml of hot hexane. Crystallization gradually took place as the solution cooled. The flask was finally cooled to −20° C. and the precipitate recovered by filtration. The solid was washed with ice cold hexanes and dried in vacuo to give 27 g (88%) of a white solid. $^1$H-NMR (CDCl$_3$): 1.23 (s, 9H), 4.53 (s, 2H), 7.2-7.5 (m, 7H), 7.68 (d, 1H).

2-Cyano-4'-methylbiphenyl

To a solution of p-bromotoluene (30 g) in dry ether (150 ml) at −78° C., a solution of t-BuLi in pentane (1.7M) (210 ml) was added slowly over a period of 1.5 hr, using a dropping funnel. The bath was then removed and the mixture was stirred at room temperature for an additional 2 hr. The contents of the flask was then added slowly (using a cannula) at room temperature to a premixed solution of ZnCl$_2$ in ether (1M) (180 ml) and dry THF (360 ml). The mixture was stirred for 2 h at that temperature and then the slurry was added (using a cannula) to a solution of 2-bromobenzonitrile (21.3 g) and NiCl$_2$(Ph$_3$P)$_2$ (2.1 g) in dry THF (300 ml). The mixture, after stirring at room temperature overnight (18 h), was poured slowly under stirring into ice-cold 1N HCl (1500 ml). The organic layer was separated, and the aqueous phase was extracted with ether (3×300 ml). The combined organic layer was washed with water, brine and then dried over MgSO$_4$. Removal of the solvent gave the crude product as a semisolid mass (34 g). The material was purified on a silica-gel flash column using ethyl acetate-hexane (1:12) to give the desired nitrile as a low-melting solid (28 g, 88%). $^1$H NMR (CDCl$_3$): 2.42 (s, 3H), 7.2–7.8 (m, 8H); FAB-MS: m/e 194 (M$^+$ +1).

Trimethylstannyl Azide

To a concentrated solution of NaN$_3$ (1.2 kg, 18.5 moles) in water (3 L), a solution of trimethyltin chloride (600 g, 3 moles) in dioxane (400 ml) was added in three portions under vigorous stirring. A precipitate formed instantaneously. The mixture, after stirring overnight at room temperature, was filtered. The residue was washed with water and dried under suction and then in vacuo over P$_2$O$_5$. Yield 541 g (88%), mp 120°–122° C.

5-[2-(4'-Methylbiphenyl)]tetrazole

To a solution of 2-cyano-4'-methylbiphenyl (390 g, 2.02 moles) in toluene (2.3 L) was added trimethyltin azide (525 g, 2.55 moles) at r.t. The mixture was refluxed for 24 h, cooled to r.t., filtered, washed with toluene and sucked dry in a funnel. The precipitate was resuspended in toluene (3.5 L) and THF (250 mL) was added. Anhydrous HCl was bubbled in at a moderate rate at r.t. to give a clear solution (45 min). Addition of HCl gas was continued for another 20 min. with stirring whereupon a white precipitate formed. The reaction mixture was stirred over night. The solid product was filtered, washed with toluene followed with ether and then dried under vacuum. This produced 250 g (53% yield of the tetrazole. m.p. 152°–154° C.; $^1$H-NMR (CDCl$_3$): 2.40 (s, 3H), 7.19 (dd, 1H), 7.55 (m, 2H), 8.25 (dd, 1H).

N-Triphenylmethyl-5-[2-(4'-methylbiphenyl)]tetrazole

To a cloudy solution of 5-[2-(4'-methylbiphenyl)]tetrazole (250 g (1.06 mole) in CH$_2$Cl$_2$ (4 L) was added triphenylmethylchloride (310 g 1.11 mole) at r.t. The reaction mixture was stirred and triethylamine (190 mL, 138 g, 1.36 mole) was added portionwise. After addition, the mixture was stirred at reflux for 90 min. The solution was cooled to r.t., washed with water (2×1 L) and dried over MgSO$_4$, filtered through a silica gel plug and concentrated on the rotovap to a solid. This was crystallized from toluene to give the product as an off-white solid (425 g, 84%); m.p. 166°–168° C.; $^1$H-NMR (CDCl$_3$): 2.28 (s, 3H), 6.9–7.05 (m, 10H), 7.2–7.5 (m, 12H), 7.9 (dd, 1H).

N-Triphenylmethyl-5-[2-(4'-bromomethylbiphenyl)]tetrazole

To a solution of N-triphenylmethyl-5-[2-(4'-methylbiphenyl)] tetrazole (425 g, 0.89 moles) in CCl$_4$ (4.0 L) were added N-bromsuccinimide (159 g, 0.89 mole) and dibenzoyl peroxide (22 g, 0.089 moles). The mixture was refluxed for 2 hours, cooled to room temperature and filtered. The filtrate was concentrated in vacuo to give a thick oil. The addition of ether (2.0 L) to this oil resulted in a clear solution. Crystallization, followed by filtration, gave a white solid (367 g, 74%). m.p. 137°–139.5° C.; $^1$H-NMR (CDCl$_3$): 4.38 (s, 2H), 6.9–8.0 (m, 23H).

N-Triphenylmethyl-5-[2-(4'-aminomethylbiphenyl)]tetrazole

To a suspension of 11.15 g (22 mmol) of N-triphenylmethyl-5-[2-(4'-bromomethylbiphenyl)]tetrazole in 55 mL of dry DMSO was added 1.23 g (25 mmol) of LiN$_3$. The mixture gradually cleared and was replaced by a new white precipitate. The mixture was stirred for 6 hours and filtered. The precipitate was washed with 50 mL of water. Some additional precipitate formed in the mixed filtrate; this was refiltered and the residue washed with 30 mL of MeOH and 100 mL of water. The solid product was dried under vacuo over night. The crude azide (9.89 g, 20.8 mmol) was dissolved in 50 ml of dry THF and treated with 5.73 g (22 mmol) of triphenylphosphine portionwise. N$_2$ evolution was observed during the addition. After 4 hours the solution was treated with 0.63 mL (34 mmol) of water and stirred over night. The solution was concentrated in vacuo and the residue purified by flash chromatography over silica gel eluting with 95:5:0.01 CHCl$_3$:MeOH:N-H$_4$OH. 6.83 g (15.4 mmol) of a white solid was recovered. 69% overall yield. $^1$H-NMR (CDCl$_3$): 3.74 (s, 2H), 6.88 (m, 5H), 7.06 (q, 4H, J=8.1 Hz), 7.22–7.52 (m, 13H), 7.95 (m, 1H).

PREPARATION OF 2-ALKYL-PYRIMIDIN-4(3H)-ONES

EXAMPLE 1

2-n-Butyl-5-ethyl-6-methylpyrimidin-4(3H)-one

A solution of 3.0 g valeramidine hydrochloride, 3.47 g ethyl 2-ethylacetoacetate, and 5.8 mL triethylamine in 20 mL DMF was heated to 120° C. for 18 hours. The mixture was diluted with brine and extracted three times with ether. The combined organic material was washed with brine, was dried over MgSO$_4$, was stripped of solvent in vacuo, and then was Still flash chromatographed in 3% MeOH in CH$_2$Cl$_2$ to give the title compound as a white solid. $^1$H NMR (300 MHz, CDCl$_3$) δ2.62 (3 line m, 2H), 2.51 (4 line m, 2H), 2.32 (s, 3H), 1.75 (m, 2H), 1.42 (6 line m, 2H), 1.10 (3 line m, 3H), 0.95 (3 line m, 3H).

EXAMPLE 2

2-n-Butyl-5,6-dimethylpyrimidin-4(3H)-one

The title compound is prepared using the procedure in Example 1 and ethyl 2-methylacetoacetate in place of ethyl 2-ethylacetoacetate.

EXAMPLE 3

2-n-Butyl-6-methylpyrimidin-4(3H)-one

A solution of 2.0 g valeramidine hydrochloride, 1.9 g ethyl acetoacetate, and 791 mg sodium methoxide in 20 mL methanol was refluxed for 24 hours. The mixture was diluted with brine and water and was extracted three times with ether. The combined organic material was washed with brine, was dried over MgSO$_4$, was stripped of solvent in vacuo, and then was Still flash chromatographed in 4% MeOH in CH$_2$Cl$_2$ to give the title compound as a white solid $^1$H NMR (250 MHz, CDCl$_3$) δ13.01 (br s, 1H), 6.18 (s, 1H), 2.67 (3 line m, 2H), 2.31 (s, 3H), 1.76 (m, 2H), 1.42 (m, 2H), 0.95 (3 line m, 3H).

EXAMPLE 4

2-n-Butyl-5-(ethoxycarbonyl)pyrimidin-4(3H)-one

To a solution of 2.0 g valeramidine hydrochloride and 750 mg sodium methoxide in 50 mL methanol was added 3.2 g diethyl ethoxymethylenemalonate (Aldrich) at room temperature. After 2 hours, an additional 850 mg sodium methoxide was added and the mixture was allowed to stir overnight. Solvent was removed in vacuo and the remaining material was partitioned between saturated aqueous ammonium chloride solution and ether. The organic layer was removed and the aqueous layer was extracted twice more with ether. The combined organic material was dried over $MgSO_4$, was stripped of solvent in vacuo, and then was Still flash chromatographed in 3% MeOH in $CH_2Cl_2$ to give the title compound as a white solid. $^1H$ NMR (250 MHz, $CDCl_3$) δ8.73 (s, 1H), 4.37 (4 line m, 2H), 2.77 (3 line m, 2H) 1.80 (m, 2H), 1.41 (m, 2H) 1.38 (3 line m, 3H), 0.96 (3 line m, 3H).

PREPARATION OF 2-ALKYL-3-ALKYL-PYRIMIDIN-4(3H)-ONES

EXAMPLE 5

2-n-Butyl-3-(2'-(N-triphenylmethyl-tetrazol-5-yl)biphen-4-yl)methyl-5-ethyl-6-methylpyrimidin-4(3H)-one To a solution of 96 mg 2-n-butyl-5-ethyl-6-methylpyrimidin-4(3H)-one in 2.5 mL THF/2.5 mL DMF was added 22 mg 60% NaH in oil. After 3 minutes 250 mg N-triphenylmethyl-5-[2-(4'-bromomethylbiphen-4-yl)]tetrazole was added. The mixture was allowed to stir overnight at room temperature then was diluted with brine and extracted three times with ether. The combined organic material was washed with brine, was dried over $MgSO_4$, was stripped of solvent in vacuo, and then was MPLC'd in 17% ethyl acetate in hexane to give the title compound as well as the O-alkylated material. The reaction produced each in about a 1:1 ratio with the N-alkylated material having the lower $R_f$. $^1H$ NMR (300 MHz, $CDCl_3$) δ7.91 (m, 1H), 7.46 (m, 2H), 7.37-7.21 (m, 12H), 7.09 (d, J=8.1 Hz, 2H), 6.93 (m, 6H), 5.19 (br s, 2H), 2.58 (4 line m, 2H), 2.51 (3 line m, 2H), 2.31 (s, 3H), 1.58 (m, 2H), 1.28 (m, 2H), 1.13 (3 line m, 3H) 0.85 (3 line m, 3H).

EXAMPLE 6

2-n-Butyl-3-(2'-(tetrazol-5-yl)-biphen-4-yl)methyl-5-ethyl-6-methylpyrimidin-4(3H)-one A solution of 2-n-butyl-3-[(2'-(N-triphenylmethyl-tetrazol-5-yl)-biphen-4-yl)-methyl]-5-ethyl-6-methylpyrimidin-4(3H)-one (from Example 5) in 4 mL acetic acid and 2 mL water was stirred at room temperature for 6 hours. The reaction mixture was diluted with brine and extracted three times with ether. The combined organic material was washed with brine, was dried over $MgSO_4$, was stripped of solvent in vacuo, and then was MPLC'd in 1 acetic acid/39 hexane/60 ethyl acetate to give the title compound as a white foam. $^1H$ NMR (300 MHz, $CDCl_3$) δ7.87 (m, 1H), 7.58 (m, 1H), 7.49 (m, 1H), 7.40 (m, 1H), 7.02 (4 line m, 4H), 5.19 (br s, 2H), 2.57 (3 line m, 2H), 2.42 (4 line m, 2H), 2.24 (s, 3H), 1.63 (m, 2H), 1.34 (m, 2H), 0.96 (3 line m, 3H), 0.88 (3 line m, 3H); IR ($CHCl_3$) 3420 (br), 3020, 1645, 1530, 1120 $cm^{-1}$; FABMS: 429 (M+1).

EXAMPLE 7

2-n-Butyl-3-(2'-cyanobiphen-4-yl)methyl-5-ethoxycarbonylpyrimidin-4(3H)-one

The title compound is prepared by stirring one equivalent of N-[(2'-cyanobiphen-4-yl)-methyl]valeramidine with diethyl ethoxymethylenemalonate (Aldrich) in a suitable solvent such as methanol or DMF. After the initial adduct is formed, one equivalent of base such as sodium methoxide is added then the material is stirred for an additional period of time, possibly with heating. Standard workup procedures appropriate to the chosen reaction solvent should be followed.

EXAMPLE 8

2-n-Butyl-3-(2'-(tetrazol-5-yl)biphenyl-4-yl)methyl-5-ethoxycarbonylpyrimidin-4(3H)-one The title compound is prepared by heating one equivalent of 2-n-butyl-3-(2'-cyanobiphen-4-yl)methyl-5-ethoxycarbonylpyrimidin-4(3H)-one from (from Example 7) with one to four equivalents of trimethylstannyl azide in toluene. After completion of the reaction the trimethylstannyl moiety is removed from the tetrazole moiety by workup with an acidic aqueous solution such as saturated aqueous ammonium chloride.

EXAMPLE 9

2-n-Butyl-3-(2'-(tetrazol-5-yl)-biphen-4-yl)methyl-5-carboxypyrimidin-4(3H)-one

The title compound is prepared by treating 2-n-butyl-3-(2'-(tetrazol-5-yl)-biphen-4-yl)methyl-5-ethoxycarbonylpyrimidin-4(3H)-one (from Example 8) with an ester hydrolyzing agent such as sodium hydroxide in an appropriate solvent such as methanol, possibly with heating. Addition of water, acidification with concentrated HCl, saturation with NaCl, extraction with ether, washing of the combined organic extracts with brine, drying of the organic material over an appropriate drying agent such as $MgSO_4$, and stripping of solvent in vacuo should give the crude organic acid which may then be purified by appropriate means such as silica gel chromatography. Alternatively, the ester from Example 8 is hydrolyzed using an appropriate esterase such as pig liver esterase followed by standard purification procedures.

EXAMPLE 10

2-n-Butyl-3-(2'-(tetrazol-5-yl)biphen-4-yl)methylpyrimidin-4(3H)-one

The title compound is prepared similarly to that in Examples 7 and 8 by using ethyl 3-ethoxyacrylate (Aldrich) in place diethyl ethoxymethylenemalonate. The procedure for converting the nitrile to the tertazole is unchanged.

EXAMPLE 11

2-n-Butyl-3-(2'-(tetrazol-5-yl)biphen-4-yl)methyl-6-methylpyrimidin-4(3H)-one

The title compound is prepared similaly to that in Example 7 and 8 by using ethyl 3-ethoxybut-2-enoate (Lancaster) in place of diethyl ethoxymethylenemalonate. The procedure for converting the nitrile to the tetrazole is unchanged.

EXAMPLE 12

2-n-Butyl-3-(2'-carboxybiphen-4-yl)methyl-6-methylpyrimidin-4(3H)-one

The title compound is prepared from N-(2'-t-butoxycarbonylbiphen-4-yl)-methylvaleramidine and ethyl 3-ethoxybut-2-enoate (Lancaster) similarly to that in Example 11. The t-butyl ester is hydrolyzed in neat trifluoroacetic acid to give the title compound.

EXAMPLE 13

2-n-Butyl-3-(2'-carboxybiphen-4-yl)methylpyrimidin-4(3H)-one

The title compound is prepared form N-(2'-t-butoxycarbonylbiphen-4-yl)methylvaleramidine and ethyl 3-ethoxyacrylate (Aldrich) similarly to that in Example 10. The t-butyl ester is hydrolyzed in neat trifluoroacetic acid to give the title compound.

EXAMPLE 14

2-n-Butyl-3-(2'-carboxybiphen-4-yl)methyl-5-ethoxycarbonylpyrimidin-4(3H)-one

The title compound is prepared form N-(2'-t-butoxycarbonylbiphen-4-yl)methylvaleramidine and diethyl ethoxymethylenemalonate (Aldrich) similarly to that in Example 7. The t-butyl ester is hydrolyzed in neat trifluoroacetic acid to give the title compound.

EXAMPLE 15

2-n-Butyl-3-(2'-carboxybiphen-4-yl)methyl-5-carboxypyrimidin-4(3H)-one

The title compound is prepared from 2-butyl-3-(2'-carboxybiphen-4-yl)methyl-5-ethoxycarbonylpyrimidin-4(3H)-one similarly to that in Example 9 by ester hydrolysis. The t-butyl ester is hydrolyzed in neat trifluoroacetic acid to give the title compound.

EXAMPLE 16

2-n-Butyl-3-(2'-(tetrazol-5-yl)-biphen-4-yl)methyl-6-ethoxypyrimidin-4(3H)-one

The title compound is prepared similarly to that in Example 7 and 8 by using ethyl 3,3-diethoxyacrylate (Aldrich) in place of diethyl ethoxymethylenemalonate. The procedure for converting the nitrile to the tetrazole is unchanged.

EXAMPLE 17

2-n-Butyl-3-(2'-carboxybiphen-4-yl)methyl-6-ethoxypyrimidin-4(3H)-one

The title compound is prepared from N-(2'-t-butoxycarbonylbiphen-4-yl)methylvaleramidine and ethyl 3,3-diethocyacrylate (Aldrich) similarly to that in Example 16. The t-butyl ester is hydrolyzed in neat trifluoroacetic acid to give the title compound.

PREPARATION OF 1-ALKYL-2-ALKYL-PYRIMIDIN-4(3H)-ONES:

EXAMPLE 18

2-n-Butyl-4-chloro-5-ethyl-6-methylpyrimidine

The pyrimidinone from Example 1 2-butyl-5-ethyl-6-methylpyrimidin-4(3H)-one is converted to the title compound upon treatment with phosphoryl chloride as described by Gabriel and Colman (Ber. 1899, 32, 2921) and by Marshall and Walker (J. Chem. Soc., 1951, 1004).

EXAMPLE 19

4-Amino-2-n-butyl-5-ethyl-6-methylpyrimidine

The title compound prepared from 2-butyl-4-chloro-5-ethyl-6-methylpyrimidine (from Example 18) upon treatment with alcoholic ammonia as described by Marshall and Walker (J. Chem. Soc., 1951, 1004).

EXAMPLE 20

2-n-Butyl-1-(2'-(N-triphenylmethyl-tetrazol-5-yl)biphen-4-yl)methyl-5-ethyl-6-methylpyrimidin-4(3H)-one The title compound is prepared by heating 4-amino-2-n-butyl-5-ethyl-6-methylpyrimidine (Example 19) with N-triphenylmethyl-5-(2-(4'-bromomethyl))tetrazole in an appropriate solvent such as methanol or DMF followed by treatment of the intermediate pyrimidinium species with aqueous base such as 0.1N sodium hydroxide as described by Brown, Hoerger, and Mason (J. Chem. Soc., 1955, 4035).

EXAMPLE 21

2-n-Butyl-1-(2'-(tetrazol-5-yl)-biphen-4-yl)methyl-5-ethyl-6-methylpyrimidin-4(3H)-one The title compound is obtained by stirring 2-n-butyl-1-(2'-(N-triphenylmethyl-tetrazol-5-yl)-biphen-4-yl)methyl-5-ethyl-6-methylpyrimidin-4(3H)-one (from Example 19) with 2:1 acetic acid/$H_2O$ for several hours as in Example 6.

EXAMPLE 22

2-n-Butyl-4-chloro-5,6-dimethylpyrimidine

The pyrimidine from Example 2 2-n-butyl-5,6-dimethylpyrimidin-4(3H)-one is converted to the title compound upon treatment with phosphoryl chloride as described by Gabriel and Colman (Ber. 1899, 32, 2921) and by Marshall and Walker (J. Chem. Soc., 1951, 1004).

EXAMPLE 23

4-Amino-2-n-butyl-5,6-dimethylpyrimidine

The title compound is prepared form 2-n-butyl-4-chloro-5,6-dimethylpyrimidine (from Example 22) upon treatment with alcoholic ammonia as described by Marshall and Walker (J. Chem. Soc., 1951, 1004).

EXAMPLE 24

2-n-Butyl-1-(2'-(N-triphenylmethyl-tetrazol-5-yl)-biphenyl-4-yl)methyl-5,6-dimethylpyrimidin-4(3H)-one The title compound is prepared by heating 4-amino-2-n-butyl-5,6-dimethylpyrimidine (from Example 23) with N-triphenylmethyl-5-(2-(4'-bromomethyl))tetrazole in an appropriate solvent such as methanol of DMF followed by treatment of the intermediate pyrimidinium species with aqueous base such as 0.1N sodium hydroxide as described by Brown, Hoerger, and Mason (J. Chem. Soc., 1955, 4035).

EXAMPLE 25

2-n-Butyl-1-(2'-(tetrazol-5-yl)-biphen-4-yl)methyl-5,6-dimethylpyrimidin-4(3H)-one The title compound obtained by stirring 2-n-butyl-1-(2'-(N-triphenylmethyl-tetrazol-5-yl)-biphen-4-yl)methyl-5,6-dimethylpyrimidin-4(3H)-one (from Example 24) with 2:1 acetic acid/$H_2O$ for several hours as in Example 6.

EXAMPLE 26

2-Butyl-4-chloro-6-methylpyrimidine

The pyrimidinone from Example 3 2-n-butyl-6-methylpyrimidin-4(3H)-one is converted to the title compound upon treatment with phosphoryl chloride as described by Gabriel amd Colman (*Ber.* 1899, 32, 2921) and by Marshall and Walker (*J. Chem. Soc.*, 1951, 1004).

EXAMPLE 27

4-Amino-2-n-butyl-6-methylpyrimidine

The title compound is prepared from 2-n-butyl-4-chloro-6-methylpyrimidine (from Example 26) upon treatment with alcoholic ammonia as described by Marshall and Walker (*J. Chem. Soc.*, 1951, 1004).

EXAMPLE 28

2-Butyl-1-(2'-(N-triphenylmethyl-tetrazol-5-yl)-biphen-4-yl)methyl-6-methylpyrimidin-4(3H)-one The title compound is prepared by heating 4-amino-2-n-butyl-6-methylpyrimidine (from Example 27) with N-triphenylmethyl-5-(2-(4'-bromomethyl))tetrazole in an appropriate solvent such as methanol or DMF followed by treatment of the intermediate pyrimidinium species with aqueous base such as 0.1N sodium hydroxide as described by Brown, Hoerger, and Mason (*J. Chem. Soc.*, 1955, 4035).

EXAMPLE 29

2-n-Butyl-1-(2'-(tetrazol-5-yl)-biphen-4-yl)methylmethylpyrimidin-4(3H)-one

The title compound is obtained by stirring 2-n-butyl-1-(2'-(N-triphenylmethyl-tetrazol-5-yl)-biphen-4-yl)methyl-6-methylpyrimidin-4(3H)-one (from Example 28) with 2:1 acetic acid/H$_2$O for several hours as in Example 6.

EXAMPLE 30

2-n-Butyl-1-(2'-carboxybiphen-4-yl)methyl-5-ethyl-6-methylpyrimidin-4(3H)-one Heating 4-amino-2-n-butyl-5-ethyl-6-methylpyrimidine (from Example 19) with 4-bromomethyl-2'-t-butoxycarbonylbiphenyl in an appropriate solvent such as methanol or DMF, followed by treatment of the intermediate pyrimidinium species with aqueous base such as 0.1N sodium hydroxide as described by Brown, Hoeger, and Mason (*J. Chem. Soc.*, 1955, 4035), followed by treatment with neat trifluoroacetic acid to achieve final deprotection of the carboxyl group, would provide the title compound.

EXAMPLE 31

2-n-Butyl-1-(2'-carboxybiphen-4-yl)methyl-5,6-dimethylpyrimidin-4(3H)-one

Heating 4-amino-2-n-butyl-5,6-dimethylpyrimidine (from Example 23) with 4-bromomethyl-2'-t-butoxycarbonylbiphenyl in an appropriate solvent such as methanol or DMF, followed by treatment of the intermediate pyrimidinium species with aqueous base such as 0.1N sodium hydroxide as described by Brown, Hoerger, and Mason (*J. Chem. Soc.*, 1955, 4035), followed by treatment with neat trifluoroacetic acid to achieve final deprotection for the carboxyl group, would provide the title compound.

EXAMPLE 32

2-n-Butyl-1-(2'-carboxybiphen-4-yl)methyl-6-methylpyrimidin-4(3H)-one

Heating 4-amino-2-n-butyl-6-methylpyrimidine (from Example 27) with 4-bromomethyl-2'-t-butoxycarbonylbiphenyl in an appropriate solvent such as methanol or DMF, followed by treatment of the intermediate pyrimidinium species with aqueous base such as 0.1N sodium hydroxide as described by Brown, Hoerger, and Mason (*J. Chem. Soc.*, 1955, 4035), followed by treatment with neat trifluoroacetic acid to achieve final deprotection of the carboxyl group, provides the title compound.

NOTE: In cases where the tetrazole moiety is to be included in the final product, it may be preformed and protected (with triphenylmethyl for example) on the biphenyl moiety prior to the condensation to form the pyrimidine.

PREPARATION OF 2-ALKYL-3-ALKYL'-6-ALKYL"-5-ARYL-PYRIMIDIN-4(3H)-ONES

EXAMPLE 33

Step 1: 2-(2-Chlorophenyl)-3-oxobutyronitrile

The procedure of P. L. Julian et al (*Org. Syn*, C. V. II, p, 487) was used. To 25 mL of anhydrous ethanol was added 2.0 g or sodium metal. The mixture was heated to 100° C. with a heating mantle to effect complete reaction. To the warm solution was added 10.0 g 2-chlorophenylacetonitrile followed by 9.7 mL dry ethyl acetate. After one hour, the mixture was cooled to −10° C. and was filtered through a medium fritted funnel. The white precipitate was washed twice with ether and was combined with the first batch. The solid material was dissolved in 75 mL water. To this was added 5 mL acetic acid. The mixture was then extracted three times with ether. The combined organic material was dried over sodium sulfate, stripped of solvent in vacuo, and was restripped from toluene to give the title compound sufficiently pure for the the next reaction. R$_f$ 0.14 in 20% ethyl acetate/hexane.

Step 2: Ethyl 2-(2-chlorophenyl)acetoacetate

The procedure of R. H. Kimball et al (*Org. Syn*, C. V. II, p. 284) was used. The curde 2-(2-chlorophenyl)-3-oxobutyronitrile from the reaction above was dissolved in 100 mL of dry ethanol and was cooled −15° C. Dry HCl was bubbled through for 30 minutes until saturated. The mixture was poured into a rapidly stirring mixture of 100 mL water and 100 mL ether. After several minutes the ether layer was removed and the aqueous layer was extracted twice more with ether. The combined organic material was washed with saturated NaHCO$_3$ solution then with saturated brine, stripped of solvent in vacuo, and MPLC'd in 20% ethyl acetate/hexane to give the title compound as a mixture of keto and enol forms. R$_f$ 0.23 in 20% ethyl acetate/hexane; $^1$H NMR (300 MHz, CDCl$_3$) δ6.50–7.17 (m, 4H), 4.23 and 4.02 (two q, 2H), 2.40 and 1.86 (two s, 3H), 1.42 and 1.19 (two t, 3H); FAB-MS: 221 and 223 (M$^+$—H$_2$O—H—).

Step 3:
2-Butyl-5-(2-chlorophenyl)-6-methylpyrimidin-4(3H)-one

A solution of 4.5 g valeramidine hydrochloride, 1.9 mg sodium methoxide, and 1.0 g ethyl 2-(2-chlorophenyl)acetoacetate in 20 mL DMF was heated to 150° C. for 20 hours. After cooling to room temperature, the reaction mixture was poured into a mixture of brine and saturated ammonium chloride solutions then was extracted three times with ether. The combined organic material was dried over MgSO$_4$, stripped of solvent in vacuo, and MPLC'd in 40% ethyl acetate/hexane to give 212 mg of the title compound as a white solid, 37% yield. R$_f$ 0.17 in 40% ethyl acetate/hexane; $^1$H NMR (300 MHz, CDCl$_3$) δ7.55 (m, 1H), 7.38 (m, 2H), 7.26 (m, 1H), 4.64 (br s, 1H), 2.74 (3 line m, 2H), 2.11 (s, 3H), 1.79 (m, 2H), 1.42 (6 line m, 2H), 0.96 (t, 3H).

Step 4:
2-Butyl-5-(2-chlorophenyl)-6-methyl-3-(2'-(tetrazol-5-yl)-biphen-4-yl)methylpyrimidin-4(3H)-one To a solution of 137 mg of 2-butyl-5-(2-chlorophenyl)-6-methylpyrimidin-4(3H)-one in 4 mL DMF was added 27 mg 60% NaH in oil. After several minutes, 250 mg N-triphenylmethyl-5-(2-(4'-bromomethylbiphenyl))tetrazole. After six hours, water was added followed by brine. This was extracted three times with ether. The combined organic material was washed with brine, dried over MgSO$_4$, stripped of solvent in vacuo, and MPLC'd in 30% ethyl acetate/hexane to give the triphenylmethyl-protected intermediate. R$_f$ 0.29 in 40% ethyl acetate/hexane.

To a solution of the triphenylmethyl-protected intermediate in methanol was added 20 drops concentrated HCl. After 20 minutes, an indicator quantity of phenolphthalein was added, followed by 10% NaOH until pink, then finally 0.5 mL acetic acid. Most of the methanol was removed in vacuo. The remaining material was diluted with brine and extracted three times with ether. The organic material was dried over MgSO$_4$, stripped of solvent in vacuo, MPLC'd in 1/7/92 acetic acid-/ethyl acetate/hexane, and stripped from toluene in vacuo to give 75 mg of the title compound as a white solid, 33% yield over two steps. R$_f$ 0.24 in 1/10/89 acetic acid/ethyl acetate/hexane; $^1$H NMR (300 MHz, CDCl$_3$) δ7.66 (m, 1H), 7.53 (m, 4H), 7.45 (m, 2H), 7.34 (m, 1H), 7.10 (4 line m, 4H), 4.65 (AB,J$_{AB}$=15.1 Hz, Δv=10.4 Hz, 2H), 2.77 (3 line m, 2H), 2.07 (s, 3H), 1.76 (m, 2H), 1.39 (m, 2H), 0.94 (t, 3H); FAB-MS: 510 and 512 (M+).

EXAMPLE 34

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| 2-Butyl-3-(2'-(tetrazol-5-yl)biphen-4-yl)-methyl-5-ethyl-6-methyl-pyrimidin-4(3H)-one | 50 |
| Lactose | 149 |
| Magnesium stearate | 1 |
| Capsule (size No. 1) | 200 |

2-n-Butyl-3-(2'-(tetrazol-5-yl)biphen-4-yl)methyl-5-ethyl-6-methylpyrimidin-4(3H)-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-n-butyl-3-(2'(tetrazol-5-yl)biphen-4-yl)methyl-5-ethyl-6-methylpyrimidin-4(3H)-one (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of 2-butyl-3-(2'(tetrazol-5-yl)biphen-4-yl)methyl-5-ethyl-6-methylpyrimidin-4(3H)-one (50 mg) pregelatinized starch USP (82 mg), microcrystalline cellulose (82 mg) and magnesium stearate (1 mg).

D: Suppository

Typical suppository formulations for rectal administration can contain 2-n-butyl-3-(2'(tetrazol-5-yl)biphen-4-yl)methyl-5-ethyl-6-methylpyrimidin-4(3H)-one (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectible formulation would contain 2-n-butyl-3-(2'(tetrazol-5-yl)biphen-4-yl)methyl-5-ethyl-6-methylpyrimidin-4-(3H)-one, sodium phosphate dibasic anhydrous (11.4 mg) benzyl alcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of formula (I):

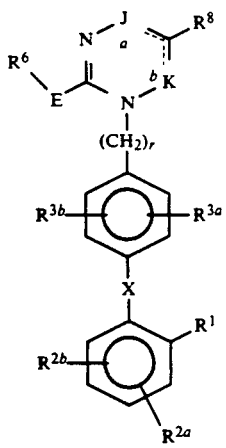

wherein:

J is —C(=M)— or

K is —C(=M)— or

provided that one and only one of J and K is —C(=M)—;

M is O or $NR^{21}$;

one of a and b is a double bond, provided that when J is —C(=M)— b is a double bond and when K is —C(=M)— a is a double bond;

$R^1$ is
(a) —$CO_2R^4$,
(b) —$SO_3R^5$,
(c) —$NHSO_2CF_3$,
(d) —$PO(OR^5)_2$,
(e) —$SO_2$—NH—$R^9$,
(f) —$CONHOR^5$,
(g)

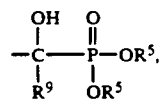

(h) —CN,
(i) —$PO(OR^5)R^4$
(j)

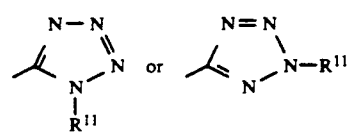

(k)

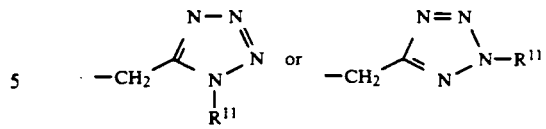

(l)

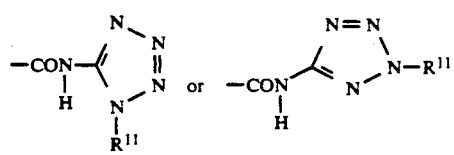

(m) —$CONHNHSO_2CF_3$,
(n)

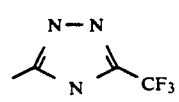

(o)

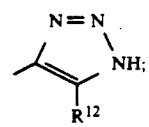

(p) $CONHSO_2R^{21}$;
(q) $SO_2NHCOR^{21}$;
(r) —$SO_2NH$-heteroaryl,
(s) —$SO_2NHCONHER^{21}$,
(t) —$CH_2SO_2NH$-heteroaryl,
(u) —$CH_2SO_2NHCO$—$R^{21}$,
(v) —$CH_2CONH$—$SO_2R^{21}$,
(w) —$NHSO_2NHCO$—$R^{21}$,
(x) —$NHCONHSO_2$—$R^{21}$, wherein heteroaryl is an unsubstituted, monosubstituted or disubstituted five- or six-membered aromatic ring which can optionally contain 1 to 3 heteroatoms selected from the group consisting of O, N or S and wherein the substituents are members selected from the group consisting of —OH, —SH, -$C_1$-$C_4$-alkyl, —$C_1$-$C_4$-alkoxy, halo (Cl, Br, F, I), —$NO_2$, —$CO_2H$, —$CO_2$-$C_1$-$C_4$-alkyl, —$NH_2$, —$NH(C_1$-$C_4$-alkyl) and —N(-$C_1$-$C_4$-alkyl)$_2$;

$R^{2a}$ and $R^{2b}$ are each independently
(a) H,
(b) halogen,
(c) $NO_2$,
(d) $NH_2$,
(e) $C_1$-$C_4$-alkylamino,
(f) di($C_1$-$C_4$-alkyl)amino
(g) $SO_2NHR^9$,
(h) $CF_3$,
(i) $C_1$-$C_6$-alkyl, $C_2$-$C_6$-alkenyl, $C_2$-$C_6$-alkynyl, or
(j) $C_1$-$C_4$-alkoxy;

$R^{3a}$ is
(a) H,
(b) halo (Cl, Br, I, F)
(c) $C_1$-$C_6$-alkyl, (d) $C_1$-$C_6$-alkoxy,
(e) $C_1$-$C_6$-alkoxy-$C_1$-$C_4$-alkyl;

$R^{3b}$ is
(a) H,
(b) halo (Cl, Br, I, F)
(c) $NO_2$,
(d) $C_1$-$C_6$-alkyl, $C_2$-$C_6$-alkenyl, $C_2$-$C_6$-alkynyl,
(e) $C_1$-$C_6$-acyloxy,
(f) $C_1$-$C_6$-cycloalkyl,
(g) $C_1$-$C_6$-alkoxy,
(h) —$NHSO_2R^4$,
(i) hydroxy $C_1$-$C_4$-alkyl,
(j) aryl-$C_1$-$C_4$-alkyl,
(k) $C_1$-$C_4$-alkylthio,
(l) $C_1$-$C_4$-alkylsulfinyl,
(m) $C_1$-$C_4$-alkylsulfonyl,
(n) $NH_2$,
(o) $C_1$-$C_4$-alkylamino,
(p) $C_1$-$C_4$-dialkylamino,
(q) perfluoro-$C_1$-$C_4$-alkyl,
(r) —$SO_2$—$NHR^9$,
(s) aryl or
(t) furyl;

wherein aryl is phenyl optionally substituted with one or two substituents selected from the group consisting of halo (Cl, Br, I, F) or $C_1$-$C_4$-alkyl optionally substituted with members selected from the group consisting of $N(R^4)_2$, $CO_2R^4$, OH, $N(R^4)CO_2R^{21}$, $S(O)_xR^{21}$ where x is 0 to 2; $C_1$-$C_4$-alkoxy, $NO_2$, $CF_3$, $C_1$-$C_4$-alkylthio, OH, $NH_2$, —$NH(C_1$-$C_4$-alkyl), —$N(C_1$-$C_4$-alkyl)_2$, —$CO_2H$, —$CO_2$-$C_1$-$C_4$-alkyl, —$N(R^4)CO_2R^{21}$ or

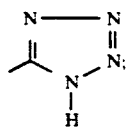

$R^4$ is H, straight chain or branched $C_1$-$C_6$-alkyl optionally substituted with aryl as defined above;
$R^{4a}$ is $C_1$-$C_6$-alkyl, aryl or aryl—$CH_2$— wherein aryl is as defined above;
$R^5$ is H,

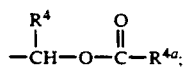

E is a single bond, —$NR^{13}(CH_2)_s$—, —$S(O)_x(CH_2)_s$— where x is 0 to 2 and s is 0 to 5, —$CH(OH)$—, —O—, CO—;

$R^6$ is
(a) aryl as defined above;
(b) straight chain or branched $C_1$-$C_6$-alkyl, $C_2$-$C_5$-alkenyl or $C_2$-$C_5$-alkynyl each of which can be optionally substituted with a substituent selected from the group consisting of aryl as defined above, $C_3$-$C_7$-cycloalkyl, halo (Cl, Br, I, F) —OH, $CF_3$, —$CF_2CF_3$, $CCl_3$, —$NH_2$, —NH(-$C_1$-$C_4$-alkyl), —$N(C_1$-$C_4$-alkyl)_2$, —NH—$SO_2R^4$, —$COOR^4$, —$SO_2NHR^9$, $C_1$-$C_4$-alkoxy, $C_1$-$C_4$-alkyl—S;
(c) an unsubstituted, monosubstituted or disubstituted heteroaromatic 5 or 6 membered cyclic ring which can contain one or two members selected from the group consisting of N, O, S, and wherein the substituents are members selected from the group consisting of —OH, —SH, $C_1$-$C_4$-alkyl, $C_1$-$C_4$-alkyloxy —$CF_3$, halo (Cl, Br, I, F), $NO_2$, —$CO_2H$, —$CO_2$-$C_1$-$C_4$-alkyl, —$NH_2$, —$NH(C_1$-$C_4$-alkyl), —$N(C_1$-$C_4$-alkyl)_2$;
(d) $C_3$-$C_7$-cycloalkyl;

$R^7$ and $R^8$ are independently
(a) H,
(b) aryl-$C_1$-$C_4$-alkyl-,
(c) heteroaryl-$C_1$-$C_4$-alkyl-,
(d) $C_1$-$C_4$-alkyl optionally substituted with a substituent selected from the group consisting of —OH, —$NH_2$, guanidino, $C_1$-$C_4$-alkoxy, —$S(O)_xR^{21}$, $C_1$-$C_4$-alkylamino, $C_1$-$C_4$-dialkylamino, —$COOR^4$, —$CON(R^4)R^{21}$, —O—$CON(R^4)R^{21}$, —O—$COR^4$, $C_3$-$C_5$-cycloalkyl, —$N(R^4)CON(R^4)R^{21}$, —$N(R^4)COOR^{21}$, —$CONHSO_2R^{21}$, —$N(R^4)SO_2R^{21}$;
(e) $C_2$-$C_4$-alkenyl,
(f) —CO-aryl as defined above,
(g) $C_3$-$C_7$-cycloalkyl,
(h) halo (Cl, Br, I, F),
(i) —OH,
(j) —$OR^{21}$,
(k) perfluro-$C_1$-$C_4$-alkyl,
(l) —SH,
(m) —$S(O)_xR^{21}$ where x is as defined above,
(n) —CHO,
(o) —$CO_2R^4$,
(p) —$SO_3H$,
(q) —$N(R^4)_2$,
(r) —$NHCO_2R^{21}$,
(s) —$SO_2NR^9R^{10}$,
(t) —$CH_2OCOR^4$,
(u) —$N(R^4)$-$SO_2$-$C_1$-$C_4$-alkyl,
(v) 5 or 6 membered saturated heterocycle containing one nitrogen atom and optionally containing one other heteroatom selected from N, O or S, such as pyrrolidine, morpholine, or piperazine,
(w) aryl as defined above,
(x) heteroaryl as defined above,
(y)

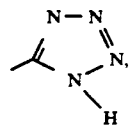

(z) —$NHSO_2$-perfluoro-$C_1$-$C_4$-alkyl,
(aa) —$CONHSO_2R^{21}$,
(bb) —$SO_2NHCOR^{21}$,
(cc) —$SO_2NH$-heteroaryl as defined above,
(dd) —$S(O)_x$-aryl as defined above,
(ee) —$S(O)_xCH_2$-aryl as defined above,
(ff) —$CON(R^4)_2$;

$R^9$ is H, $C_1$-$C_5$-alkyl, phenyl or benzyl;
$R^{10}$ is H, $C_1$-$C_4$-alkyl;
$R^{11}$ is H, $C_1$-$C_6$-alkyl, $C_2$-$C_4$-alkenyl, $C_1$-$C_4$-alkoxy alkyl, or —$CH_2$—$C_6H_4R^{20}$;
$R^{12}$ is —CN, —$NO_2$ or —$CO_2R^4$;
$R^{13}$ is H, $C_1$-$C_4$-acyl, $C_1$-$C_6$-alkyl, allyl, $C_3$-$C_6$-cycloalkyl, phenyl or benzyl;
$R^{14}$ is H, $C_1$-$C_8$-alkyl, $C_1$-$C_8$-perfluoroalkyl, $C_3$-$C_6$-cycloalkyl, phenyl or benzyl;
$R^{15}$ is H, $C_1$-$C_6$-alkyl;
$R^{16}$ is H, $C_1$-$C_6$-alkyl, $C_3$-$C_6$-cycloalkyl, phenyl or benzyl;

$R^{17}$ is $-NR^9R^{10}$, $-OR^{10}$, $-NHCONH_2$, $-NHCSNH_2$,

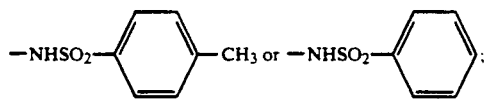

$R^{18}$ and $R^{19}$ are independently $C_1$–$C_4$-alkyl or taken together are $-(CH_2)_q-$ where q is 2 or 3;

$R^{20}$ is H, $-NO_2$, $-NH_2$, $-OH$ or $-OCH_3$;

$R^{21}$ is
  (a) aryl as defined above;
  (b) heteroaryl as defined above;
  (c) $C_1$–$C_6$-alkyl optionally substituted with a substituent selected from the group consisting of aryl as defined above, heteroaryl as defined above, $-OH$, $-NH_2$, $-NH(C_1$–$C_4$-alkyl), $-N(C_1$–$C_4$-alkyl)$_2$, $-CO_2H$, $-CO_2R^4$, halo (Cl, Br, F, I), $-CF_3$;
  (d) $C_3$–$C_5$-cycloalkyl;

X is
  (a) a carbon-carbon single bond,
  (b) $-CO-$,
  (c) $-O-$,
  (d) $-S-$,
  (e)

(f)

(g)

(h) $-OCH_2-$,
  (i) $-CH_2O-$,
  (j) $-SCH_2-$,
  (k) $-CH_2S-$,
  (l) $-NHC(R^9)(R^{10})$,
  (m) $-NR^9SO_2-$,
  (n) $-SO_2NR^9-$,
  (o) $-C(R^9)(R^{10})NH-$,
  (p) $-CH=CH-$,
  (q) $-CF=CF-$,
  (r) $-CH=CF-$,
  (s) $-CF=CH-$,
  (t) $-CH_2CH_2-$,
  (u) $-CF_2CF_2-$,
  (v)

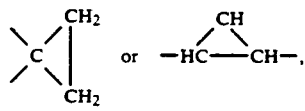

(w)

(x)

(y)

(z)

or

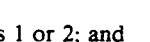

r is 1 or 2; and
the pharmaceutically acceptable salts thereof.

2. A compound of claim 1 wherein:
J is $-C(=M)-$;
K is

b is a double bond;
$R^1$ is
  (a) CCOH,
  (b)

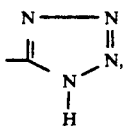

(c)

(d) $-NH-SO_2CF_3$,
  (e) $-CO_2R^4$,
  (f) $CONHSO_2R^{21}$;
  (g) $SO_2NHCOR^{21}$;
  (h) $-SO_2NH$-heteroaryl,
  (i) $-SO_2NHCONHR^{21}$,
  (j) $-CH_2SO_2NH$-heteroaryl,
  (k) $-CH_2SO_2NHCO-R^{21}$
  (l) $-CH_2CONH-SO_2R^{21}$,
  (m) $-NHSO_2NHCO-R^{21}$,
  (n) $-NHCONHSO_2-R^{21}$, $R^{2a}$ and $R^{2b}$ are H, F, Cl, $CF_3$ or $C_1$–$C_6$-alkyl;
$R^{3a}$ is H;
$R^{3b}$ is H, F, Cl, $CF_3$, $C_1$–$C_6$-alkyl. $C_5$–$C_6$-cycloalkyl, $-COOCH_3$, $-COOC_2H_5$, $-SO_2-CH_3$, $NH_2$, $-N(C_1$–$C_4$-alkyl)$_2$ or $-NH-SO_2CH_3$;

E is a single bond, —O— or —S—;
R⁶ is
(a) $C_1$-$C_5$-alkyl optionally substituted with a substituent selected from the group consisting of Cl, $CF_3$, $CCl_3$, —O—$CH_3$, —$OC_2H_5$, —S—$CH_3$, —S—$C_2H_5$ or phenyl;
(b) $C_2$-$C_5$-alkenyl or $C_2$-$C_5$-alkynyl;
R⁷ and R⁸ are independently
(a) H,
(b) $C_1$-$C_4$-alkyl,
(c) $C_2$-$C_4$-alkenyl,
(d) —OH,
(e) —$CH_2OCOR^4$,
(f) —$NH_2$,
(g)

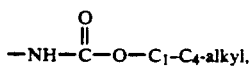

(h) -$C_1$-$C_4$-alkoxy,
(i) —NH($C_1$-$C_4$-alkyl)$_2$,
(j) —N($C_1$-$C_4$-alkyl)$_2$,
(k) halo (Cl, F, Br),
(l) —$CF_3$,
(m) —$CO_2R^4$,
(n) —$CH_2$—OH,
(o) 5 or 6 membered saturated heterocycle containing one nitrogen atom and optionally containing one other heteroatom selected from N, O, or S, such as pyrrolidine, morpholine, or piperazine;
(p) —CO-aryl as defined above,
(q) —S(O)$_x$-$C_1$-$C_4$-alkyl;
(r) —$SO_2$—NH-$C_1$-$C_4$-alkyl,
(s) —$SO_2$—NH-aryl as defined above,
(t) —NH—$SO_2CH_3$,
(u) aryl as defined above;
(v) heteroaryl as defined above;
(w)

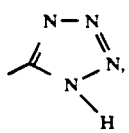

X is a C—C single bond or —CO—; and,
r is one.
3. A compound of claim 2 wherein:
E is a single bond or —S—;
r is one,
$R^{2a}$, $R^{2b}$, $R^{3a}$ and $R^{3b}$ are each H;
R⁶ is n-propyl, n-butyl, —$CH_3$, —$CH_2CH_3$, or —$CH_2$—S—$CH_3$;
R⁷ is —$CHSO_2CF_3$, —$CH_2OH$, —$CH_2OCOR^4$, —$CO_2R^4$, —N($CH_3$)$_2$, —$NHCO_2$—$C_1$-$C_4$-alkyl,

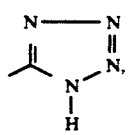

H, —$C_1$-$C_4$-alkyl, aryl, or a 5 or 6 membered saturated heterocycle as defined above;
R⁸ is H, —$C_1$-$C_4$-alkyl, aryl, heteroaryl, Cl, F, $CF_3$;
R¹ is (a) —COOH,
(b)

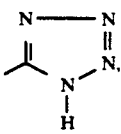

(c)

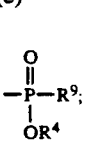

(d) —NH—$SO_2$—$CF_3$,
(e) $CONHSO_2R^{21}$;
(f) $SO_2NHCOR^{21}$;
(g) —$SO_2$NH-heteroaryl,
(h) —$SO_2NHCONHR^{21}$,
(i) —$CH_2SO_2NH$-heteroaryl,
(j) —$CH_2SO_2NHCO$—$R^{21}$,
(k) —$CH_2CONH$—$SOR^{21}$,
(l) —$NHSO_2NHCO$—$R^{21}$,
(m) —$NHCONHSO_2$—$R^{21}$,
X is a single bond.
4. A compound of claim 3 selected from the group consisting of:

(1) 2-n-Butyl-1-(2'-(tetrazol-5-yl)-biphen-4-yl)methyl-pyrimidin-4(1H)-one;
(2) 2-n-Butyl-1-(2'-(tetrazol-5-yl)biphen-4-yl)methyl-5,6-dimethylpyrimidin-4(1H)-one;
(3) 2-n-Butyl-1-(2'-(tetrazol-5-yl)biphen-4-yl)methyl-6-hydroxymethyl-5-phenylpyrimidin-4-(1H)-one;
(4) 2-n-Butyl-1-(2'-(tetrazol-5-yl)biphen-4-yl)methyl-5-(2-chloro)phenyl-6-hydroxymethylpyrimidin-4(1H)-one;
(5) 2-n-Butyl-1-(2'-(tetrazol-5-yl)biphen-4-yl)methyl-5-chloro-6-hydroxymethylpyrimidin-4(1H)-one;
(6) 2-n-Butyl-1-(2'-(tetrazol-5-yl)biphen-4-yl)methyl-6-carboethoxypyrimidin-4(1H)-one;
(7) 2-n-Butyl-1-(2'-(tetrazol-5-yl)biphen-4-yl)methyl-6-carboethoxy-5-(2-chloro)phenylpyrimidin-4-(1H)-one;
(8) 2-n-Butyl-1-(2'-(tetrazol-5-yl)biphen-4-yl)methyl-5-(2,5-dichloro)phenyl-6-hydroxymethylpyrimidin-4-(1H)-one;
(9) 2-n-Butyl-1-(2'-(tetrazol-5-yl)biphen-4-yl)methyl-6-acetoxymethyl-5-(2-chloro)phenylpyrimidin-4-(1H)-one;
(10) 2-n-Butyl-1-(2'-(tetrazol-5-yl)biphen-4-yl)methyl-5-(2-carboethoxy)phenylpyrimidin-4-(1H)-one;
(11) 2-n-Butyl-1-(2'-(tetrazol-5-yl)biphen-4-yl)methyl-5-(2-carboethoxy)phenyl-6-methylpyrimidin-4-(1H)-one;
(12) 2-n-Butyl-1-(2'-(tetrazol-5-yl)biphen-4-yl)methyl-5-(2-carboxy)phenyl-6-methylpyrimidin-4-(1H)-one;
(13) 2-n-Butyl-1-(2'-(tetrazol-5-yl)biphen-4-yl)methyl-5-(2-carboxy)phenyl-6-dimethylaminopyrimidin-4-(1H)-one;
(14) 2-n-Butyl-1-(2'-(carboxy)biphen-4-yl)methyl-pyrimidin-4-(1H)-one;
(15) 2-n-Butyl-1-(2'-(carboxy)biphen-4-yl)methyl-6-(tetrazol-5-yl)pyrimidin-4-(1H)-one;

(16) 2-n-Butyl-1-(2'-(carboxy)biphen-4-yl)methyl-5-methyl-6-(tetrazol-5-yl)pyrimidin-4-(1H)-one;

(17) 2-n-Butyl-1-(2'-(carboxybiphen-4-yl)methyl)-5-(2-chloro)phenyl-6-(tetrazol-5-yl)pyrimidin-4(1H)-one;

(18) 2-n-Butyl-1-(2'-(tetrazol-5-yl)biphen-4-yl)methyl-5-(2-chloro)phenyl-6-(tetrazol-5-yl)pyrimidin-4(1H)-one;

(19) 2-Butyl-6-carboxy-5-(2-chloro)phenyl-1-(2'-(N-(1,3,5-triazin-2-yl)sulfamido)biphen-4-yl)methyl-pyrimidin-4(1H)-one;

(20) 2-Butyl-6-carbomethoxy-5-(2-chloro)phenyl-1-(2'-N-1,3-5-triazin-2-yl)sulfamido)biphen-4-yl)methyl-pyrimidin-4(1H)-one;

(21) 2-Butyl-6-carboxy-5-(2-chloro)phenyl-1-(2'-(N(pyrimidin-2-yl)sulfamido)biphen-4-yl)methyl-pyrimidin-4(1H)-one;

(22) 1-(2'-(N-Acetylsulfamido)biphen-4-yl)methyl-2-butyl-6-carboxy-5-(2-chloro)phenylpyrimidin-4(1H)-one;

(23) 1-(2'-(N-Benzoylsulfamido)biphen-4-yl)methyl-2-butyl-6-carboxy-5-(2-chloro)phenylpyrimidin4(1H)-one;

(24) 2-Butyl-6-carboxy-5-(2-chloro)phenyl-1-(2'-(N-trifluoroacetylsulfamido)biphen-4-yl)methylpyrimidin-4(1H)-one;

(25) 2-Butyl-6-carboxy-5-(2-chloro)phenyl-1-(2'-((N-methylsulfonyl)carboxamido)biphen-4-yl)methyl-pyrimidin-4(1H)-one;

(26) 2-Butyl-6-carboxy-5-(2-chloro)phenyl-1-(2'-((N-phenylsulfonyl)carboxamido)biphen-4-yl)methyl-pyrimidin-4(1H)-one;

(27) 2-Butyl-6-carboxy-5-(2-chloro)phenyl-1-(2'-((N-morpholin-4-phenylsulfonyl)carboxamido)biphen-4-yl)methyl-pyrimidin-4(1H)-one;

(28) 2-Butyl-6-carboxy-5-(2-chloro)phenyl-1-(2'-((N-(dimethylamino)sulfonyl)carboxamido)biphen-4-yl)methylpyrimidin-4(1H)-one; and

(29) 6-Carboxy-2-cyclopropyl-5-(2-chloro)phenyl-1-(2'-(tetrazol-5-yl)biphen-4-yl)methylpyrimidin-4(1H)-one.

5. A compound of claim 1 wherein:
K is —C(=O)—;
J is

a is a double bond;
$R^7$ is
  (a) —COOH,
  (b)

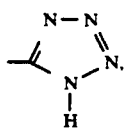

(c)

(d) —NH—SO$_2$CF$_3$,
(e) CO$_2$R$^4$,
(f) CONHSO$_2$R$^{21}$;
(g) SO$_2$NHCOR$^{21}$;
(h) —SO$_2$NH-heteroaryl,
(i) —SO$_2$NHCONHR$^{21}$,
(j) —CH$_2$SO$_2$NH-heteroaryl,
(k) —CH$_2$SO$_2$NHCO—R$^{21}$,
(l) —CH$_2$CONH—SO$_2$R$^{21}$,
(m) —NHSO$_2$NHCO—R$^{21}$,
(n) —NHCONHSO$_2$—R$^{21}$, $R^{2a}$ and $R^{2b}$ are H, F, Cl, CF$_3$, C$_1$-C$_6$-alkyl, C$_2$-C$_6$-alkenyl, C$_2$-C$_6$-alkynyl;
$R^{3a}$ is H, F or Cl;
$R^{3b}$ is H, F, Cl, CF$_3$, C$_1$-C$_6$-alkyl, C$_2$-C$_6$-alkenyl, C$_2$-C$_6$-alkynyl, C$_5$-C$_6$-cycloalkyl, —COOCH$_3$, —COOC$_2$H$_5$, —SO$_2$—CH$_3$, —N(R$^4$)$_2$ or —NH—SO$_2$CH$_3$;
E is a single bond, —O— or —S—;
$R^6$ is
  (a) C$_1$-C$_5$-alkyl optionally substituted with a substituent selected from the group consisting of Cl, CF$_3$, CCl$_3$, —O—CH$_3$, —OC$_2$H$_5$, —S—CH$_3$, —S—C$_2$H$_5$ or phenyl;
  (b) C$_2$-C$_5$-alkenyl or C$_2$-C$_5$-alkynyl;
  (c) C$_3$-C$_5$-cycloalkyl;
$R^7$ and $R^8$ are independently
  (a) H,
  (b) C$_1$-C$_4$-alkyl optionally substituted with —N(R$^4$)CO$_2$R$^{21}$, —S(O)$_x$R$^{21}$, aryl, —N(R$^4$)$_2$, —CO$_2$R$^4$, —N(R$^4$)CON(R$^4$)R$^{21}$, —CON(R$^4$)R$^{21}$;
  (c) C$_2$-C$_4$-alkenyl,
  (d) —OH,
  (e) —CH$_2$OCOR$^4$,
  (f) —NH$_2$,
  (g) —N(R$^4$)COOR$^{21}$,
  (h) —C$_1$-C$_4$-alkoxy,
  (i) —NH(C$_1$-C$_4$-alkyl),
  (j) —N(C$_1$-C$_4$-alkyl)$_2$,
  (k) halo(Cl, F, Br),
  (l) —CF$_3$,
  (m) —CO$_2$R$^4$,
  (n) —CH$_2$—OH,
  (o) 5 or 6 membered saturated heterocycle as defined above,
  (p) —CO-aryl as defined above,
  (q) —S(O)$_x$—C$_1$-C$_4$-alkyl
  (r) —SO$_2$—NH—C$_1$-C$_4$-alkyl,
  (s) —SO$_2$—NH-aryl as defined above,
  (t) —NH—SO$_2$CH$_3$,
  (u) aryl as defined above;
  (v) heteroaryl as defined above;
  (w)

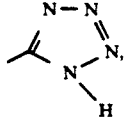

X is a C—C single bond or —CO—; and,
r is one.

6. A compound of claim 5 wherein:
E is a single bond or —S—;
r is one,
$R^1$ is (a) —CO$_2$R$^4$
(b) —CONHSO$_2$R$^{21}$,
(c) —NHSO$_2$CF$_3$,
(d) —SO$_2$NHCOR$^{21}$,
(e) —SO$_2$NH-heteroaryl,
(f)

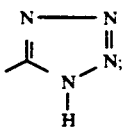

R$^{2a}$ and R$^{2b}$ are H, F, Cl, CF$_3$, C$_1$–C$_6$-alkyl, C$_2$–C$_6$-alkenyl, C$_2$–C$_6$-alkynyl;
R$^{3a}$ is H, F, or Cl;
R$^{3b}$ is H, F, Cl, CF$_3$, C$_1$–C$_6$-alkyl, C$_2$–C$_6$-alkenyl, C$_2$–C$_6$-alkynyl, C$_5$–C$_6$-cycloalkyl, —COOCH$_3$, —COOC$_2$H$_5$, —SO$_2$—CH$_3$, —N(R$^4$)$_2$ or —NH—SO$_2$CH$_3$;
R$^6$ is n-propyl, n-butyl, —CH$_2$CH$_3$, cyclopropyl or cyclopropylmethyl,
X is a single bond or —CO—.

7. A compound of claim 6 selected from the group consisting of:

(1) 2-n-Butyl-3-(2'-(tetrazol-5-yl)biphen-4-yl)methylpyrimidin-4(3H)-one;
(2) 2-n-Butyl-3-(2'-(tetrazol-5-yl)biphen-4-yl)methyl-5,6-dimethylpyrimidin-4(3H)-one;
(3) 2-n-Butyl-3-(2'-(tetrazol-5-yl)biphen-4-yl)methyl-5-ethoxycarbonyl-6-phenylpyrimidin-4-(3H)-one;
(4) 2-n-Butyl-3-(2'-(tetrazol-5-yl)biphen-4-yl)methyl-5-ethoxycarbonyl-6-ethylpyrimidin-4-(3H)-one;
(5) 2-n-Butyl-3-(2'-(tetrazol-5-yl)biphen-4-yl)methyl-6-(2-chloro)phenyl-5-hydroxymethylpyrimidin-4(3H)-one;
(6) 2-n-Butyl-3-(2'-(tetrazol-5-yl)biphen-4-yl)methyl-6-chloro-5-hydroxymethylpyrimidin-4(3H)-one;
(7) 2n-Butyl-3-(2'-(tetrazol-5-yl)biphen-4-yl)methyl-6-dimethylamino-5-hydroxymethylpyrimidin-4(3H)-one;
(8) 2n-Butyl-3-(2'-(tetrazol-5-yl)biphen-4-yl)methyl-6-dimethylamino-5-ethylpyrimidin-4(3H)-one;
(9) 2-n-Butyl-3-(2'-(tetrazol-5-yl)biphen-4-yl)methyl-6-acetoxymethyl-5-(2-chloro)phenylpyrimidin-4(3H)-one;
(10) 2-n-Butyl-3-(2'-(tetrazol-5-yl)biphen-4-yl)methyl-6-ethyl-5-phenylpyrimidin-4(3H)-one;
(11) 2-n-Butyl-3-(2'-(tetrazol-5-yl)biphen-4-yl)methyl-5-ethyl-6-(2-chloro)phenylpyrimidin-4(3H)-one;
(12) 2-n-Butyl-3-(2'-(tetrazol-5-yl)biphen-4-yl)methyl-5-(2-carboxy)phenyl-6-ethyl-pyrimidin-4(3H)-one;
(13) 2-n-Butyl-3-(2'-(tetrazol-5-yl)biphen-4-yl)methyl-5-(2-carboethoxyphenyl)-6-ethylpyrimidin-4(3H)-one;
(14) 2-n-Butyl-3-(2'-(carboxy)biphen-4-yl)methyl-5-(2-(tetrazol-5-yl))phenyl-6-ethylpyrimidin-4(3H)-one;
(15) 2-n-Butyl-3-(2'-(tetrazol-5-yl)biphen-4-yl)methyl-5-[2-(tetrazol-5-yl)]phenyl-6-ethylpyrimidin-4(3H)-one;
(16) 2-n-Butyl-3-(2'-(tetrazol-5-yl)biphen-4-yl)methyl-5-(tetrazol-5-yl)-6-ethyl-pyrimidin-4(3H)-one;
(17) 2-n-Butyl-3-(2'-carboxybiphen-4-yl)methyl-5-(tetrazol-5-yl)-6-ethylpyrimidin-4(3H)-one;
(18) 2-Butyl-5-(2-chloro)phenyl-6-methyl-3-(2'-(N-phenylsulfonyl)carboxamido)biphen-4-yl)methylpyrimidin-4(3H)-one;
(19) 2-Butyl-5-(2-chloro)phenyl-6-methyl-3-(2'-(N-(methyl-sulfonyl)carboxamido)biphen-4-yl)methylpyrimidin-4(3H)-one;
(20) 2-Butyl-5-(2-chloro)phenyl-6-methyl-3-(2'-(N-(trifluoromethylsulfonyl)carboxamido)biphen-4-yl)methylpyrimidin-4(3H)-one;
(21) 2-Butyl-5-(2-chloro)phenyl-6-methyl-3-(2'-(N-(morpholin-4-yl)sulfonylcarboxamido)biphen-4-yl)methyl)pyrimidin-4(3H)-one;
(22) 3-(2'-(N-Acetylsulfamido)biphen-4-yl)methyl-2-butyl-5-(2-chloro)phenyl-6-methylpyrimidin-4(3H)-one;
(23) 3-(2'-N-Benzoylsulfamido)biphen-4-yl)methyl-2-butyl-5-(2-chloro)phenyl-6-methylpyrimidin-4(3H)-one;
(24) 2-Butyl-5-(2-chloro)phenyl-6-methyl-3-(2'-(N-trifluoroacetylsulfamido)biphen-4-yl)methylpyrimidin-4(3H)-one;
(25) 2-Butyl-5-(2-chloro)phenyl-6-methyl-3-(2'-(N-(pyrimidin-2-yl)sulfamido)biphen-4-yl)methylpyrimidin-4(3H)-one;
(26) 2-Butyl-5-(2-chloro)phenyl-6-methyl-3-(2'-(N-(1,3-5-triazin-2-yl)sulfamido)biphen-4-yl)methylpyrimidin-4(3H)-one;
(27) 2-Butyl-5-(2-chloro)phenyl-6-methyl-3-(2'-(N-(1,2,4-oxadiazol-3-yl)sulfamido)biphen-4-yl)methylpyrimidin-4(3H)-one;
(28) 3-(5'-allyl-2'-(tetrazol-5-yl)biphen-4-yl)methyl-2-butyl-5-(2-chloro)phenyl-6-methylpyrimidin-4(3H)-one;
(29) 2-Butyl-5-(2-chloro)phenyl-6-methyl-3-(5'-propyl-2'-(tetrazol-5-yl)biphen-4-yl)methylpyrimidin-4(3H)-one;
(30) 5-(2-Chloro)phenyl-2-cyclopropyl-6-methyl-3-(5'-propyl-2'-(tetrazol-5-yl)biphen-4-yl)methylpyrimidin-4(3H)-one;
(31) 2-Butyl-3-(4'-chloro-2'-(tetrazol-5-yl)biphen-4-yl)methyl-5-(2-chloro)phenyl-6-methylpyrimidin-4(3H)-one;
(32) 2-Butyl-5-(2-chloro)phenyl-6-methyl-3-(5'-phenyl-2'-(tetrazol-5-yl)biphen-4-yl)methylpyrimidin-4(3H)-one;
(33) 2-Butyl-5-(2-chloro)phenyl-6-methyl-3-(5'-(4-methyl)phenyl-2'-(tetrazol-5-yl)biphen-4-yl)methylpyrimidin-4(3H)-one;
(34) 5-(2-Chloro)phenyl-2-cyclopropyl-6-methyl-3-(5'-(4-methyl)phenyl-2'-(tetrazol-5-yl)biphen-4-yl)methylpyrimidin-4(3H)-one; and
(35) 5-(2-Chloro)phenyl-2-cyclopropyl-6-methyl-3-(5'-propyl-2'-((N-benzoyl)sulfonamido)biphen-4-yl)methylpyrimidin-4(3H)-one.

8. A compound of claim 1 wherein:
K is —C(=NR$^{21}$);
J is

a is a double bond;
R$^1$ is
(a) —COOH,
(b)

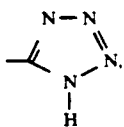

(c)

(d) —NH—SO$_2$CF$_3$,
(e) CO$_2$R$^4$,
(f) CONHSO$_2$R$^{21}$;
(g) SO$_2$NHCOR$^{21}$;
(h) —SO$_2$NH-heteroaryl,
(i) —SO$_2$NHCONHR$^{21}$,
(j) —CH$_2$SO$_2$NH-heteroaryl,
(k) —CH$_2$SO$_2$NHCO—R$^{21}$,
(l) —CH$_2$CONH—SO$_2$R$^{21}$,
(m) —NHSO$_2$NHCO—R$^{21}$,
(n) —NHCONHSO$_2$—R$^{21}$, R$^{2a}$ and R$^{2b}$ are H, F, Cl, CF$_3$ C$_1$-C$_6$-alkyl, C$_2$-C$_6$-alkenyl, C$_2$-C$_4$-alkynyl;

R$^{3a}$ is H, F or Cl;

R$^{3b}$ is H, F, Cl, CF$_3$, C$_1$-C$_6$-alkyl, C$_2$-C$_6$-alkenyl, C$_2$-C$_6$-alkynyl, C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$, —NH—SO$_2$CH$_3$, E is a single bond —O— or —S—;

R$^6$ is (a) C$_1$-C$_5$-alkyl optionally substituted with a substituent selected from the group consisting of Cl, CF$_3$, CCl$_3$, —O—CH$_3$, —OC$_2$H$_5$, —S—CH$_3$, —S—C$_2$H$_5$ or phenyl;

(b) C$_2$-C$_5$-alkenyl or C$_2$-C$_5$-alkynyl;

R$^7$ and R$^8$ are independently (a) H,
(b) C$_1$-C$_6$-alkyl,
(c) C$_2$-C$_6$-alkenyl,
(d) —OH,
(e) —CH$_2$OCOR$^4$,
(f) —NH$_2$,
(g)

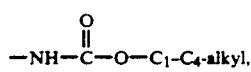

(h) —C$_1$-C$_4$-alkoxy,
(i) —NH(C$_1$-C$_4$-alkyl),
(j) —N(C$_1$-C$_4$-alkyl)$_2$,
(k) halo(Cl, F, Br),
(l) —CF$_3$,
(m) —CO$_2$R$^4$,
(n) —CH$_2$—OH,
(o) 5 or 6 membered saturated heterocycle as defined above,
(p) —CO-aryl as defined above,
(q) —S(O)$_x$—C$_1$-C$_4$-alkyl
(r) —SO$_2$—NH—C$_1$-C$_4$-alkyl,
(s) —SO$_2$—NH-aryl as defined above,
(t) —NH—SO$_2$CH$_3$,
(u) aryl as defined above;

(v) heteroaryl as defined above;
(w)

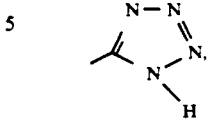

X is a C—C single bond or —C—; and,
r is one.

9. A compound of claim 8 wherein:
E is a single bond or —S—;
r is one,
R$^{2a}$, R$^{2b}$, R$^{3a}$ and R$^{3b}$ are each H;
R$^6$ is n-propyl, n-butyl, —CH$_3$, or —CH$_2$CH$_3$;
R$^7$ and R$^8$ are independently selected from: H, C$_1$-C$_6$-alkyl, —Cl, C$_1$-C$_4$-alkoxy, —F, —CH$_2$OH, NO$_2$, —CO$_2$R$^4$—NH—COO—C$_1$-C$_4$-alkyl, —CF$_3$, —CH$_2$OCOR$^4$, —NH$_2$, —NH(C$_1$-C$_4$-alkyl), —N(-C$_1$-C$_4$-alkyl)$_2$,

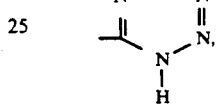

aryl or a 5 or 6 membered saturated heterocycle as defined above;
X is a single bond or —CO—.

10. A compound of cliam 9 selected from the group consisting of:

(1) N-Methyl 2-butyl-5-(2-chloro)phenyl-6-methyl-3-(2'-(tetrazol-5-yl)biphen-4-yl)methylpyrimidin-4(3H)-imine;

(2) N-Ethyl 2-butyl-5-(2-chloro)phenyl-6-methyl-3-(5'-propyl-2'-(tetrazol-5-yl)biphen-4-yl)methylpyrimidin-4(3H)-imine;

(3) N-Propyl 2-cyclopropyl-6-methyl-3(2'-(tetrazol-5-yl)biphen-4-yl)methyl-5-(2-trifluoromethyl)phenylpyrimidin-4(3H)-imine;

(4) N-Phenyl 2-butyl-5-(2-chloro)phenyl-6-methyl-3-(2'-(tetrazol-5-yl)biphen-4-yl)methyl-pyrimidin-4(3H)-imine;

(5) N-Benzyl 2-butyl-5(2-chloro)phenyl-6-methyl-3(2'-(tetrazol-5-yl)biphen-4-yl)methylpyrimidin-4(3H)-imine;

(6) N-Carboxymethyl 2-butyl-5-(2-chloro)phenyl-6-methyl-3(2'-(tetrazol-5-yl)biphen-4-yl)methylpyrimidin-4(3H)-imine;

(7) N-(Pyridin-2-yl) 5-(2-chloro)phenyl-2-cyclopropyl-6-methyl-3-(5'-(4-methyl)phenyl-2'-(tetrazol-5-yl)biphen-4-yl)methylpyrimidin-4(3H)-imine; and (8) N-Cyclopropyl 3-(2'-((N-benzoyl)sulfonamido)biphen-4-yl)methyl-2-butyl-5-(2-chloro)phenyl-6-methylpyrimidin-4(3H)-imine.

11. A pharmaceutical composition useful in the treatment of hypertension which comprises a pharmaceutically acceptable carrier and a pharmaceutically effective amount of a compound of claim 1.

12. A method of treating hypertension which comprises administering to a patient in need of such treatment a pharmaceutically effective amount of a compound of claim 1.

13. An ophthalmological formulation for the treatment of ocular hypertension comprising an ophthalmologically acceptable carrier and an effective ocular antihypertensive amount of a compound of claim 1.

14. A method of treating ocular hypertension comprising administering to a patient in need of such treatment an effective ocular antihypertensive amount of a compound of claim 1.

* * * * *